(12) United States Patent
Chatterjee et al.

(10) Patent No.: US 11,384,354 B2
(45) Date of Patent: Jul. 12, 2022

(54) METHOD OF GENERATING AN ANTIBODY NAÏVE LIBRARY, SAID LIBRARY AND APPLICATION(S) THEREOF

(71) Applicant: ZUMUTOR BIOLOGICS, INC., Woburn, MA (US)

(72) Inventors: Sohang Chatterjee, Lexington, MA (US); Kavitha Iyer Rodrigues, Bangalore (IN); Maloy Ghosh, Bangalore (IN); Sunit Maity, Bangalore (IN); Divya Unnikrishnan, Bangalore (IN); Yogendra Manjunath Bangalore Muniraju, Bangalore (IN); Sathyabalan Murugesan, Bangalore (IN); Pavithra Mukunda, Kundapur (IN); Bhargav Prasad, Tamil Nadu Chennai (IN); Veeresha Kamanagowda, Bangalore (IN); Sanghamitra Bhattacharjee, Bangalore North Bangalore (IN); Pravin Kumar Dakshinamurthy, Chennai (IN); Vivek Halan, Tamil Nadu Aravenu (IN); Sankaranarayanan Srinivasan, Bangalore (IN); Anuradha Hora, Uttar Pradesh Sitapur (IN);

(Continued)

(73) Assignee: ZUMUTOR BIOLOGICS INC., Woburn, MA (US)

( * ) Notice: Subject to any disclaimer, the term of this patent is extended or adjusted under 35 U.S.C. 154(b) by 933 days.

(21) Appl. No.: 16/065,003

(22) PCT Filed: Dec. 21, 2015

(86) PCT No.: PCT/IB2016/057872
§ 371 (c)(1),
(2) Date: Jun. 21, 2018

(87) PCT Pub. No.: WO2017/109721
PCT Pub. Date: Jun. 29, 2017

(65) Prior Publication Data
US 2020/0283757 A1   Sep. 10, 2020

(30) Foreign Application Priority Data
Dec. 21, 2015   (IN) .......................... 6808/CHE/2015

(51) Int. Cl.
*C12N 15/10*   (2006.01)
*C07K 16/00*   (2006.01)
(Continued)

(52) U.S. Cl.
CPC ........ *C12N 15/1037* (2013.01); *C07K 16/005* (2013.01); *C12Q 1/686* (2013.01); *C40B 50/06* (2013.01)

(58) Field of Classification Search
CPC .. C12N 15/1037; C07K 16/005; C12Q 1/686; C40B 50/06
See application file for complete search history.

(56) References Cited

U.S. PATENT DOCUMENTS

2013/0085072 A1    4/2013   Bradbury et al.
2014/0331343 A1*  11/2014  Bradley ................. C40B 50/06
                                              800/18
2017/0029811 A1*   2/2017   Weiner ............... C12N 15/1037

FOREIGN PATENT DOCUMENTS

WO    99/36569 A2    7/1999
WO    03/029456 A1   4/2003
(Continued)

OTHER PUBLICATIONS

Sblattero (Nat. Biotech., 2000, 18:75-80) (Year: 2000).*
(Continued)

*Primary Examiner* — Jeremy C Flinders
(74) *Attorney, Agent, or Firm* — Hamre, Schumann, Mueller & Larson, P.C.

(57) ABSTRACT

The present disclosure relates to a method of generating an antibody library, not limiting to a human naïve antibody
(Continued)

gene expression library encompassing a pool of nucleic acid sequences derived from a natural antibody repertoire comprising humoral immunity from healthy and genetically diverse human populations. More specifically, the method employs a combination of phage and/or yeast antibody surface display concept which allows to screen large antibody library size and facilitates better folding of antibody structure. The present disclosure also relates to a human naïve antibody library generated by employing the process of the present disclosure, a set of primers employed in the method and application(s) of said antibody library.

19 Claims, 16 Drawing Sheets

Specification includes a Sequence Listing.

(51) Int. Cl.
    *C12Q 1/686*   (2018.01)
    *C40B 50/06*   (2006.01)
    *A61P 3/00*    (2006.01)

(72) Inventors: Bairavabalakumar Natarajan, Tamil Nadu Chennai (IN); Karthika Nair, Karnataka Bangalore (IN); Aswini Thanigaivel, Tamil Nadu Chennai (IN); Amol Maliwalave, Karnataka Bangalore (IN); Bharath Ravindra Shenoy, Bangalore (IN); Sahana Bhima Rao, Karnataka Bangalore (IN); Subhra Prakash Chakrabarty, Karnataka Bangalore (IN); Ashvini Kumar Dubey, Vidyaranyapura Bangalore (IN); Amir Khan, Uttar Pradesh Aligarh (IN); Anurag Tiwari, Lamni Badalalpur Varanasi (IN); Santosh Kumar, Jharkhand Charki Giridih (IN); Shivani Patel, Madhya Pradesh Adhartal (IN); Nikitha M, Karnataka Bangalore (IN)

(56) References Cited

FOREIGN PATENT DOCUMENTS

| WO | 2007/047578 A2 | 4/2007 |
| WO | 2008/100816 A2 | 8/2008 |
| WO | 2015/089080 A2 | 6/2015 |

OTHER PUBLICATIONS

Buck et al. (BioTechniques, 1999, 27:528-536 (Year: 1999).*
Feldhaus et al. (Nat. Biotech., 2003, 21:163-170) (Year: 2003).*
Gietz et al. (Yeast, 1995, 11:355-360) (Year: 1995).*
Fortunato Ferrara et al. "Using Phage and Yeast Display to Select Hundreds of Monoclonal Antibodies: Application to Antigen 85, a Tuberculosis Biomaker," PLOS One, vol. 7, No. 11, Nov. 2012, pp. e49535.
Ridder R et al. "Generation of Rabbit Monoclonal Antibody Fragments from a Combinatorial Phage Display Library and Their Production in the Yeast *Pichia pastoris*," Bio/Technology. The International Monthly for Industrial Biology, Nature Publishing Group, US, vol. 13, No. 3, Mar. 1995, pp. 255-260.
Boder Eric T et al. "Directed evolution of antibody fragments with monovalent femtomolar antigen-binding affinity," Proceedings National Academy of Sciences PNAS, National Academy of Sciences, US, vol. 97, No. 20, Sep. 2000, pp. 10701-10705.
Boder Eric T et al. "Yeast Surface Display for Screening Combinatorial Polypeptide Libraries," Nature Biotechnology, Gale Group Inc., US, vol. 15, Jun. 1997, pp. 553-557.
Iba Y et al. "Expression vectors for the introduction of highly diverged sequences into the six complementarity-determining regions of an antibody," Gene, Elsevier, NL, vol. 194, No. 1, Jul. 1997, pp. 35-46.
Rajpal A et al. "A general method for greatly improving the affinity of antibodies by using combinatorial libraries," Proceedings National Academy of Sciences PNAS, National Academy of Sciences, US, Jun. 2005, pp. 8466-8471.
Monegal Ana et al. "Immunological applications of single-domain llama recombinant antibodies isolated from a naïve library," Protein Engineering, Design and Selection, Oxford Journal, GB, vol. 22, No. 4, 2009, pp. 273-280.
Hutchings C et al. "Chapter 6, Generation of Naive Antibody Libraries," Antibody Engineering, Jan. 2001, pp. 93-108.
Vinita Puri et al. "Highly efficient selection of epitope specific antibody through competitive yeast display library sorting," mAbs, vol. 5, No. 4, Jul. 2013, pp. 533-539.
International Search Report and Written Opinion issued in PCT/IB2016/057872, dated May 19, 2017, 24 pages.
Written Opinion of the International Preliminary Examining Authority issued in PCT/IB2016/057872, dated Mar. 28, 2018, 8 pages.

\* cited by examiner

A.

B.

C.

D.

A.

B.

METHOD OF GENERATING AN ANTIBODY NAÏVE LIBRARY, SAID LIBRARY AND APPLICATION(S) THEREOF

TECHNICAL FIELD

The present disclosure generally relates to the field of biotechnology, genetic engineering and immunology. Particularly, the present disclosure relates to a method of generating an antibody library, not limiting to a human naïve antibody gene expression library encompassing a pool of nucleic acid sequences derived from a natural antibody repertoire comprising humoral immunity from healthy and genetically diverse human populations. More specifically, the method employs a combination of phage and/or yeast antibody surface display concept which allows to screen large antibody library size and facilitates better folding of antibody structure. The present disclosure also relates to a human naïve antibody library generated by employing the process of the present disclosure, a set of primers employed in the method and application(s) of said antibody library

BACKGROUND OF THE DISCLOSURE

Human monoclonal antibody (mAb) and their derivatives are one of the largest and fastest growing segments of biopharmaceutical industry. Recent application of recombinant DNA technology for generating and expressing antibodies has attained a significant amount of interest among scientists from industry and academia.

Chimeric, humanized and human mAb, the prevailing formats of therapeutic mAb, share human constant domains but are discerned by the origin of their variable domains. Human mAb have a set of variable domains that are entirely stemmed from human antibody repertoires. Chimeric antibodies are artificially developed using the human codon usage which might result in anti-antibody response. This is one of the most important therapeutic limitations of early monoclonal antibody therapy. Moreover, this development of immune response can affect its efficacy and safety for example, reduced target binding, altered clearance and pharmacokinetics. Furthermore, humanized antibodies yielded from humanization process of the antibodies or grafting of CDR sequences bind antigen differently than the parent antibody. Thus, human monoclonal antibodies are generally viewed to have better pharmacokinetic and pharmacodynamic features when compared to monoclonal antibodies from nonhuman antibody repertoires. Immunogenicity of humanized mAbs is substantially less in comparison with nonhuman and chimeric monoclonal antibodies.

Approaches such as immunization and murine hybridoma technology are traditionally followed for generation of antibodies. However, limitations of immunization have been with safety and pharmacokinetic properties which directly impact utility and efficacy of drug molecule development. Limitations of hybridoma technology have been with the antigens' toxicity or non-immunogenicity in mice. Considering the high sequence homologies between the human and the respective murine antigen, generation of antibodies to self-antigens can be challenging.

More specifically, limitations associated with hybridoma technology are multifactorial. There is no control over the epitopes to which antibodies are formed. Antibodies must be screened extensively after they are created in the hope that one has been created with characteristics that are desirable to the investigator. Moreover, Sensitive antigens (e.g. membrane proteins and nucleic acids) could be destroyed in the animal while toxic antigens might kill the animal. Considering the high sequence homology between the human and the mice, respective murine antigen might give rise to non-immunogenicity in mice wherein generation of antibodies to self-antigens can be challenging. The scope of further development of antibodies in terms of rationally introducing features exhibiting higher affinity is extremely limited and difficult to do.

Human antibody repertoires that are collections of human immunoglobulin (Ig) genes that encode human heavy and light chains include VH, D, JH and CH gene segments of the heavy chain locus on chromosome 14; Vk, Jk and Ck gene segments of the kappa light chain locus on chromosome 2; and Vλ, Jλ and Cλ gene segments of the lambda light chain locus on chromosome 22 in the human genome. The natural immune response in vivo generates a variety of antibody molecules, with low to moderate affinity towards antigen, via antigen-independent recombination processes such as VHDJH, VkJk and VλJλ joining processes. All of V, D and J gene joining processes such as, VH-D, D-JH, Vk-Jk and Vλ-Jλ, follow one inviolable rule that relates to the structure of their recognition sequence either one-turn and two-turn recognition sequences which give rise to either in-phase or out-phase joints resulting diversity in immune repertoire. The process of V(D)J recombination is initiated by VDJ recombinase, which exists in multiple forms. The crucial enzymes mediating the process are Recombination Activating Genes 1 and 2 (RAG), Terminal deoxynucleotidyl Transferase (TdT), and Artemis nuclease. Artemis nuclease is a member of the ubiquitous non-homologous end joining (NHEJ) pathway and functions in DNA repair. All these joining gene's segments are flanked by recombination signal sequences (RSSs) comprising of conserved heptamer and nonamer elements while separated by spacers of either 12 or 23 base pairs. The recombination process is initiated by RAG1 and RAG2 proteins and high mobility group proteins, by assembling a pair of dissimilar RSSs into a synaptic complex (the 12/23 rule) and generates double-strand DNA breaks between the RSSs and coding segments. The physiological substrates of the V(D)J recombination machinery comprises of three distinct immunoglobulin (Ig) loci, Igh, Igk and Igl, and three distinct T cell receptor (TCR) loci, Tcrb, Tcra/Tcrd and Tcrg. This tightly regulated recombination process proceeds within the context of similar developmental programs in the B and T cell lineages. The assembly proceeds firstly, with D to J rearrangement followed by V to DJ rearrangement. In-frame rearrangements lead to the assembly of pre-receptors, which signal a down-regulation of RAG expression results a burst of proliferation and a developmental transition toward a second stage of RAG expression. In this stage, pre-B cells undergo Vκ to Jκ and Vλ to Jλ rearrangement. In both B and T cell lineages, V(D)J recombination is terminated by a cessation of RAG expression.

Diversity via rearrangements of genes occurs during B-lymphocyte maturation in an orderly manner. Somatic hyper mutation or SHM is one of the DNA transactions that contribute to the generation of antibody diversity in mammalian B lymphocytes. Another crucial process which is involved in diversity addition is class switching recombination (CSR). In CSR, the Cµ region is replaced by Cγ, CE, or Ca segments to generate IgG, IgE, and IgA antibodies, respectively. This process is facilitated by an intra-chromosomal recombination event between the switch (S) region of the Cµ region (Sµ) and one of the downstream S regions. These S regions are located immediately upstream of each of the C regions (except for δ) and contain imperfect G-C-rich pentameric repeats that serve as the donors and recipients for a recombination process. Interestingly, CSR is region specific not sequence specific. The SHM is specific to V-region with changes having single base substitutions, with occasional insertions and deletions. There are potential hot spots for the mutations although there are no preferences for locations suggesting that other local sequences or higher-order structures may influence the targeting of mutations. The rate of SHM is $\sim 10^{-5}$ to $10^{-3}$ mutations per base pair per generation which is $\sim 10^6$-fold higher than the spontaneous rate of mutation in most other genes where transition mutations arise more frequently than do transversions. Antibody repertoire has been found biased towards many diseases, from infections to autoimmune disorders to cancers. There is a possibility of heritable variation in the composition of the antibody repertoire which could alter inherent risk to specific diseases. However, the characterization of heritable influences on diversity of the antibody repertoire remains to be deciphered.

Also, new and advanced naïve or non-immune library with careful selection of donors from diverse genetic background is not yet available. Large and diverse human antibody libraries are associated with several advantages which can be used, explored and improved against several antigens whereby resulting animal immunization can be bypassed. Antibodies may be generated against toxic or low immunogenic antigens upon immunization. Furthermore, in contrast to murine monoclonal antibodies, the risk of allergic response can be diminished with the use of human antibodies. The diversity of the library determines the probability to isolate an antibody with high affinity and efficacy for a given antigen. Therefore, several studies in the art are underway and techniques exist, which are directed towards generating large and diverse human antibody libraries.

Antibodies are glycoproteins and act as a critical part of the immune response by specifically recognizing and binding to particular antigens, such as bacteria or viruses and aiding in efficient destruction. Antibodies are of various isotypes and differ in their structure, biological features, target specificity and distribution. Hence the assessment of the Antibody isotypes and diversity can provide useful insight into complex humoral immune response. There are several ways to increase antibody diversity such as random shuffling of the heavy and light chain genes, by altering the complementarity determining region 3 (CDR3) of the cloned heavy chain genes of the library, and by introducing polymerase chain reactions (PCR) based mutations. Immunoglobulins are categorized in two different forms i) soluble; ii) membrane bound. The first antigen receptors expressed by B cells are IgM and IgD, prototype of the antibody that the B cell is tuned to produce. The B cell receptor (BCR) can only bind antigens. It is the heterodimer of Ig alpha and Ig beta that enables the cell to transduce the signal and respond to the presence of antigens on the cell surface. The signal causes the growth and proliferation of the B cell and antibody production inside the cell. The various antibodies produced by plasma cells are classified into isotypes that differ in function and antigen responses primarily due to structure variability. In placental mammals, there are five major isotypes that have been identified: IgA, IgD, IgG, IgE and IgM. Antibody isotypes are categorized according to differences in their amino acid sequence in the constant region (Fc) of the antibody heavy chains. The Immunoglobulins IgG and IgA are further grouped into subclasses (e.g. in Human IgG1, IgG2, IgG3, IgG4, IgA1 and IgA2) based on additional small differences in the amino acid sequences. Based on differences in the amino acid sequence in the constant region of the light chain, immunoglobulins can also be sub-classified into two; kappa light chain or lambda light chain. As a part of adaptive immunity, B cells primarily provide the humoral response through specific antibody secretion to address invading bodies and their toxic products. The B cells can undergo a "class switch" that causes expression of a new antibody isotype. As exemplified, the antibody isotype could switch from an IgM to an antibody of all possible classes (e.g. IgG1, IgG4, IgE). During this switch, the constant region of the heavy chain is changed, while the variable regions of the heavy chain remain unchanged. This switch does not affect the antibody's specificity for its antigen, but it does alter the effector functions that each class of antibody can execute. Disease states can range from the absence of one isotype class or subclass to a total deficiency of immunoglobulin classes. Auto-immune diseases and gastro intestinal conditions are characterized by specific isotype deficiencies or varying concentrations of one or more isotypes. In the context of library backbone development and generation of Fab format, IgG1 isotype is preferred. IgG antibodies are most common and abundant in circulation representing 75% of the serum antibodies, precisely a crucial reason for therapeutic antibodies to adopt the constant domains. Based on its abundance in serum, IgG has been further classified in to 4 sub-categories; IgG1, IgG2, IgG3 and IgG4. Among four sub-groups, IgG1 is the most abundant IgG with 66%. In addition, properties such as ability to cross placenta easily, significant complement activation capability, extremely high affinity with Fc receptor on phagocytes and highest half-life made IgG1 a preferred backbone to develop therapeutic monoclonal antibodies.

Naive libraries are made via utilizing the inbuilt diversity of antibody genes in multiple donors. Overlap extension PCR were used to prepare a cDNA library prepared from peripheral blood B cell which were combined within a selected framework of the DP-47 germline gene (VH3 family). The antibody diversity produced with this process is completely different from naturally created in the immune system in one individual, meaning that this approach could give rise to new type of antibody molecule with higher therapeutic potential. Among various formats, genes encoding single chain antibody (ScFv) or Fab were made by randomly combining heavy and light chain V-genes using PCR and the combinatorial library could be cloned in phagemids or yeast vectors for display on the surface of a phage or yeast.

There remains a general need in the art for antibody library generation with an increased diversity which will enable the rapid selection and production of therapeutic antibodies with higher affinity and improved functionality against specific antigen molecule.

Major strategies for mining human antibody repertoires are: a) non-combinatorial and b) combinatorial strategies. Non-combinatorial strategies retrieve human mAbs from single B-cells with the original heavy and light chain pairs while combinatorial strategies involve human antibody library with randomly combined heavy and light chains. Both approaches have led to food and drug administration (FDA) and European medical agency (EMA) approved human mAbs. Among non-combinatorial approaches, the adaptation of hybridoma technology to the generation of human mAbs has seen sincere efforts over years, however, has been a slow and difficult process due to the limited number of B-cells stimulated with an antigen of interest and due to lack of its genetic stability. Therefore, generating viable hybridomas is typically challenging for practical applications and has not become a popular choice for mining human antibody repertoires. In contrast, combinatorial mining of human antibody repertoires is intertwined with Bcell mRNA rather than B-cells showcasing a compartmental or physical linkage of phenotype (protein) and genotype (cDNA). The success of display selection relies on the ability to retrieve the genetic information along with the functional protein. Several devised and validated display methods are available such as cell based and cell-free. Among several display and protein interaction systems that have been established as selection methods for antibody-antigen interaction, most preferred are via display of the antibody on the surface of, either phages, yeast or on ribosomes following an in vitro transcription. However, each of these display and protein interaction systems are associated with respective advantages and drawbacks.

Phage display was first established by Smith and coworkers, wherein heterologous expression of peptides was achieved on filamentous phage. Various antibody formats can be expressed efficiently in the periplasmic space of *E. coli*. There are two kinds of phage display systems, one, phage vector and other being the phagemid based display system. The phage vector system consists of the entire phage genome with the antibody gene inserted as a fusion to a phage surface protein. On the other hand, phagemid system consists of two components: a phagemid carrying the phage surface protein-antibody fusion and helper phage, aiding the assembly of phage. Phagemid system has a major advantage when compared to phage system as the smaller vector size and ease of cloning, allows accommodating large library sizes. The main difference between both systems lies in the display level of the antibodies. The display on phagemid systems is monovalent with antibodies being carried on the surface while every phage produced by a phage vector system carries 3-5 copies of the antibody on its surface (multivalent display). Moreover, the multivalent display of phage vector system is used for avidity effect during selection against antigen while monovalent display of phagemid system is linked with more of stringency or affinity related selection. Regarding the formats of antibody displayed on phage is mostly ScFv or Fab; however, due to lack of any post translational modification, full length Ig expression is difficult. Phage display is the most accepted method due to ease of cloning, allowing for large library sizes, monovalent display and easy to determine various stability parameters. However, with phage display there are associated limitations on proper protein folding due to it being a prokaryotic expression system and lack of post translational modifications of the displayed antibody fragments thereby. Therefore, although phage display has few advantages, such as robustness, as well as certain limitations, yet it has become one of the most frequently used display methods for combinatorial antibody libraries.

On the other hand, yeast surface display of ScFv antibodies was first instituted by Boder and Wittrup in 1997 while its applicability for the selection against antigen from large libraries was shown by Feldhaus and coworkers. In contrast to phage display, full length IgGs can successfully be displayed on yeast cells. The major advantage of yeast display platform is its compatibility with FACS allowing one to select antibodies against antigens mimicking the natural condition and also parameters such as antibody expression levels, number of bound antigen, or cross-reactivities can be determined in parallel. However, yeast and similarly all other eukaryotic cell surface systems is restricted by the limited transformation efficiency setting limits on the library size that can be achieved.

Furthermore, cell-free methodology includes an in-vitro transcription followed by displaying on ribosomes. The concept of ribosome display was brought in by Mattheakis and coworkers while established and validated by Hanes and Pluckthun as a selection method for antibody ScFv fragments. The Ribosome display method is technically more challenging due to relative instability of the RNA and the ribosomal complex. Therefore, the key feature of ribosome display is the generation of stable protein-ribosome-mRNA (PRM) complexes via ribosome stalling in such that the nascent protein and mRNA remain associated. There are two different strategies that are used to stabilize the complex i) use of antibiotics to stop translation; ii) depletion of stop codon to stall the ribosome, as this invites release factors followed by detachment of nascent protein thereby destabilizing the complex. One of the major advantages of this system is to accommodate the size of the library without the restriction of transformation. However, limitation of this technique is to display a single chain protein such as ScFv.

Therefore, each of these display and protein interaction systems is associated with respective merits and demerits.

Since the mid-1990s, antibodies have emerged as an important new drug class. So far, 18 antibodies are now approved for therapeutic purposes in the United States across diverse clinical settings, including various areas such as chronic inflammatory diseases, oncology, transplantation, cardiovascular medicine and infectious diseases. At least >150 additional therapeutic antibodies drugs are in various stages of clinical development. Therapeutic antibody belongs to a well-established drug class with a high success rate: 29% for chimeric antibodies and 25% for humanized antibodies comparing with a success rate of ~11% for small molecule drugs. In general, tolerance of antibodies is well taken for humans, although first dose of infusion reactions are common but manageable.

A key strength of antibodies as therapeutics is that their clinical potential can readily be increased by improving their existing properties. Antibodies have numerous inter-dependent properties that can be tuned to improve their clinical potential such as immunogenicity, antigen binding specificity and affinity, effector functions and other biological activities, pharmacokinetics, molecular architecture, internalization after cell binding, and biophysical properties. All antibodies, including protein drugs, are potentially immunogenic. Generally, it has been seen that patients commonly develop a mouse-antibody-specific antibody response when administered mouse antibodies, such as acceleration of clearance, direct neutralization, induction of serum sickness and prevention of further dosing. Antibody immunogenicity often depends on the primary amino-acid structure aggregated or mis-folded antibody or contaminants, heterogeneity in the antibody pool and the presence of T-cell epitopes. Antibody immunogenicity is also influenced by multitude of clinical parameters, including the dose, route and frequency of administration and patient-specific factors, such as disease and immune status, MHC haplotype and concomitant medication.

A prerequisite for targeted therapy demand that antibodies should typically bind their target antigen with highly specific selectivity. Success at generating such species cross-reactive antibodies depends on the sequence-relatedness of the antigen in different species (including the conservation of the target epitope) and the method of antibody generation.

Antibody display technology circumvent the induction of immune tolerance and allow screening or preferably, direct selection for species cross-reactivity. Successful application of antibodies in therapy includes high affinity as a key attribute. The functional aspect of many antibodies is dictated by stoichiometric blockade of a target protein, so higher affinity enables a longer duration of effect for a given dose of drug. It is essential to understand the amino acid compositional biases in CDR segments that are most appropriate for high affinity antigen interactions. To improve antibody affinity by mutation, there are practical limitations on the number of variant sequences that can be generated and tested.

Many library-construction strategies, in conjunction with several display technologies, have been used successfully for the affinity maturation of antibodies such as screening a phage-display library to increase the affinity of an HIV-1 glycoprotein 120 (gp120)-specific monoclonal antibody fragment and an ERBB2 (HER2)-specific monoclonal antibody fragment from the nanomolar to the picomolar range. Similar successes have been observed with the use of phage-display libraries and with the use of yeast- and ribosome-display libraries. Separate mutations that increase binding affinity are routinely combined and often further increase affinity in an additive or synergistic manner.

Few other key attributes of the variable domains of antibodies differ widely in biophysical properties such as stability, solubility and folding kinetics. By using antibody display libraries for the selection of antibody fragments with optimized binding activity, favorable properties such as robust expression, high stability and solubility are often selected together. Direct selection for favorable biophysical properties can be achieved using chemical denaturants, high temperature and reducing agents or proteases.

The instant disclosure aims to overcome limitations associated with different display platforms. Combinatorial libraries in comparison with non-combinatorial approach, are derived from a large number of VH genes and VL genes, wherein the number of possible combinations might give rise to newly formed combinations and might exhibit antigen-specific binding activity that is reasonably strong. The success of these libraries solely depends on the final library size which should be sufficiently large. The instant disclosure therefore aims to create highly diverse antibody gene library which is capable of accommodating a large library size, which can thereby improve the potential of generating lead molecules against antigenic targets.

STATEMENT OF THE DISCLOSURE

Accordingly, the present disclosure relates to a method of generating antibody naïve library comprising processing biological sample(s) to isolate nucleic acid(s) followed by amplification, pooling of the amplified product(s) and cloning of antibody genes into phage to obtain phage antibody library followed by screening of displayed genes against antigen(s) to obtain panned phage antibody library or pooling of the amplified product(s) and cloning of antibody genes directly into yeast to obtain yeast antibody library displaying the antibody genes on surface of the yeast; followed by screening the displayed genes against antigen(s) to obtain screened yeast antibody library, transferring the panned phage antibody library of the phage library into yeast for display of said antibody genes on surface of yeast followed by screening the yeast displayed antibody genes against antigen(s) to obtain yeast screened antibody library, and selecting the phage or the yeast displayed antibodies/genes with desired functional properties which form the naïve antibody library or isolating selected antibodies with desired functional properties from the phage antibody library or the yeast antibody library to generate screened antibody naïve library; the present disclosure also relates to a naïve antibody library obtained by the method as above; the present disclosure also relates to primer sequence(s) set forth as any of SEQ ID 1 to 68 wherein the primer sequence(s) is employed for obtaining the naïve antibody library as above or carrying out the method as above for generating/obtaining the naïve antibody library; and the present disclosure also relates to a naïve antibody library as above or as obtained by method as above for use in therapeutics for treatment of diseases selected from a group comprising cancer, rheumatoid arthritis, neurological disorders, infectious diseases and metabolic disorders or any combination thereof; as diagnostics; as prognostics; for research purposes; target discovery; validation in functional genomics or any application where antibodies or derivatives of antibodies are employed.

BRIEF DESCRIPTION OF THE ACCOMPANYING FIGURES

The features of the present disclosure will become fully apparent from the following description taken in conjunction with the accompanying figures. With the understanding that the figures depict only several embodiments in accordance with the disclosure and are not to be considered limiting of its scope, the disclosure will be described further through use of the accompanying figures.

Figure 6:
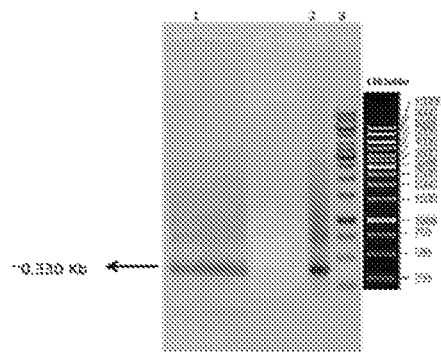
Figure 6:
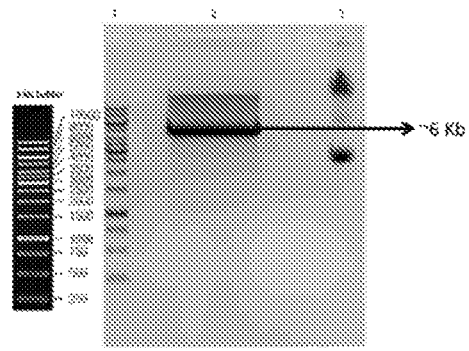
Figure 6:
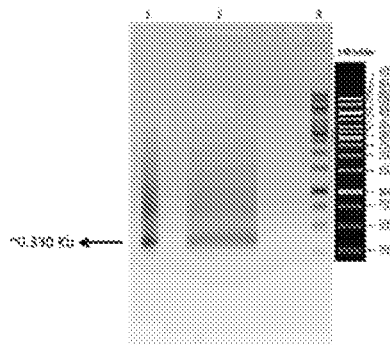
Figure 6:
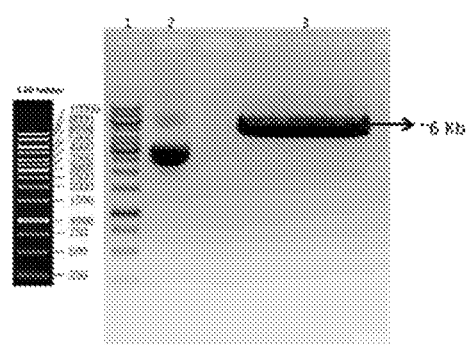

FIG. 6 illustrate Restriction digestion of vectors and inserts. A. Digestion of Kappa pool of clones, B. Digestion of Kappa vector, C. Digestion of Lambda pool of clones, D. Digestion of Lambda vector.

Figure 7:
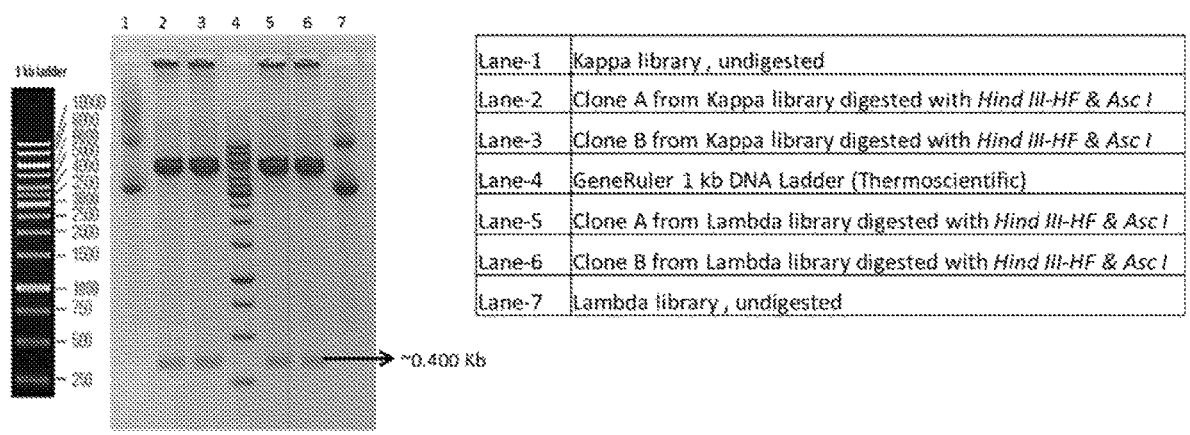

FIG. 7 illustrate Analysis of independent clones from Kappa library and Lambda library using HindIII-HF and AscI enzymes and run on 1% agarose gel.

Figure 8:
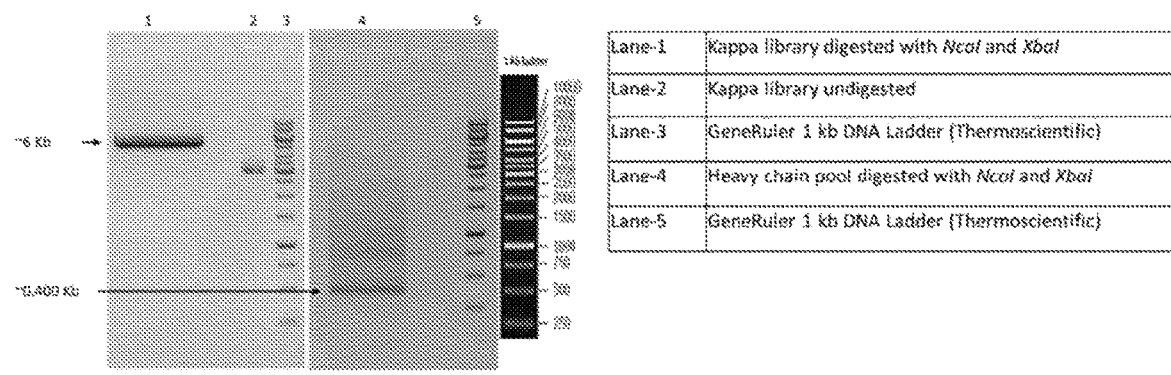
Figure 8:
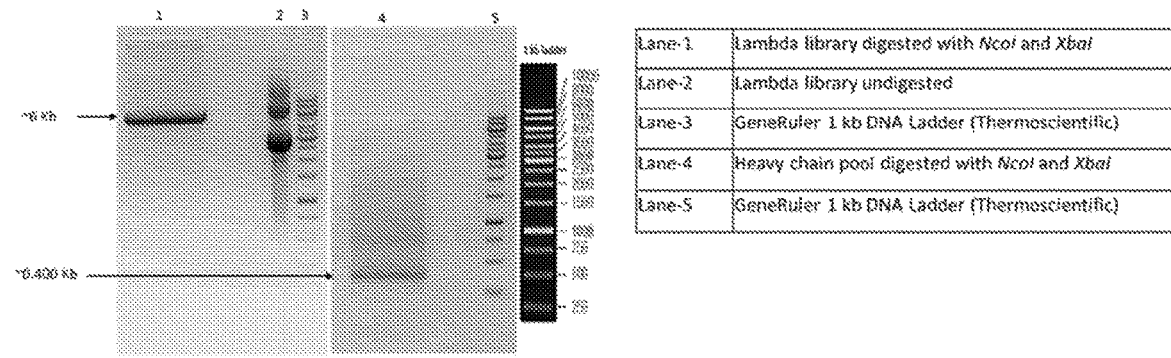

FIG. 8 illustrates Restriction digestion with NcoI and XbaI to clone heavy chain pool in (A) Kappa library and (B) Lambda library and run on 1% agarose gel.

Figure 9:
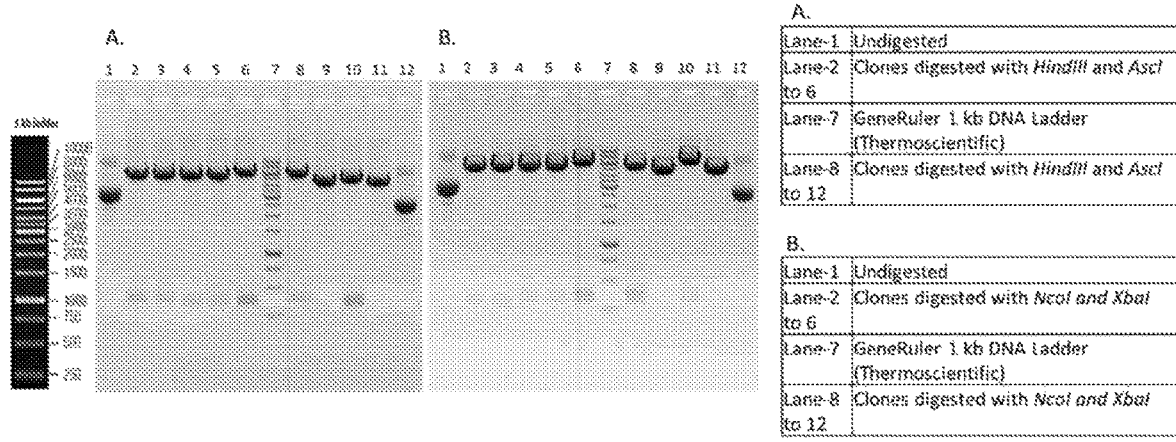

FIG. 9 illustrates Restriction digestion analysis of independent clones A. Digestion with HindIII and AscI to confirm Light chain Kappa insert, B. Digestion with NcoI and XbaI to confirm Heavy chain insert.

Figure 10:
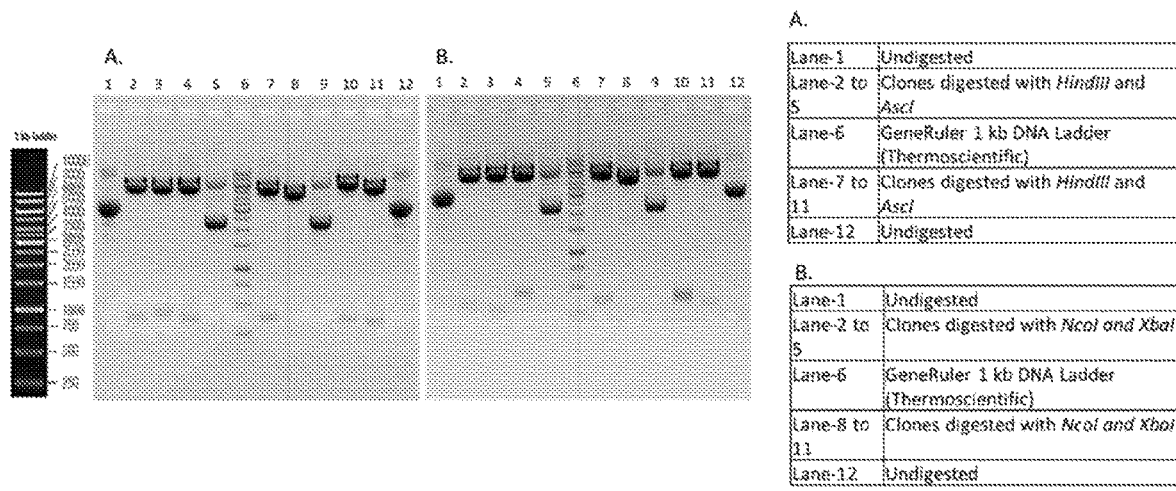

FIG. 10 illustrates Restriction digestion analysis of independent clones A. Digestion with HindIII and AscI to confirm Light chain Lambda insert, B. Digestion with NcoI and XbaI to confirm Heavy chain insert.

Figure 11:
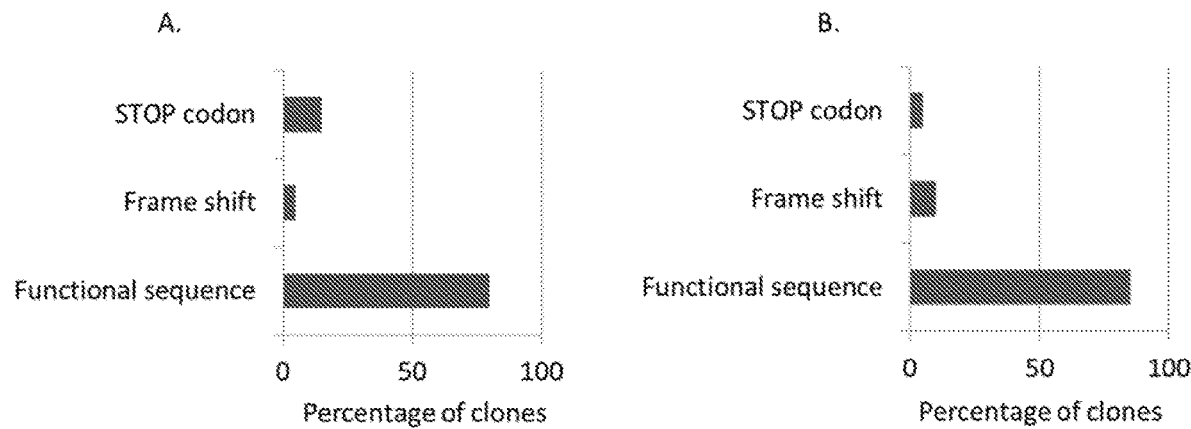

FIG. 11 illustrates Sequence correctness of the antibody gene libraries. (A) Heavy chain library, (B) Kappa and Lambda chain libraries.

Figure 12:
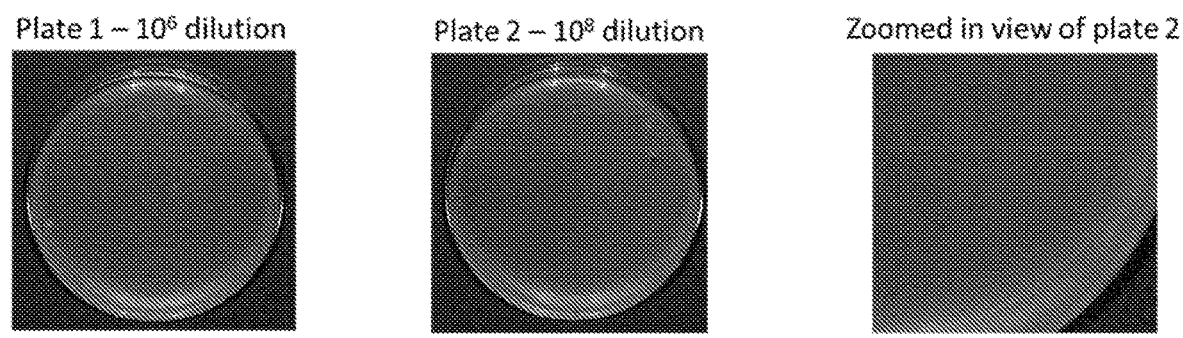

FIG. 12 illustrate Plaque assay of Antibody gene library.

Figure 13:
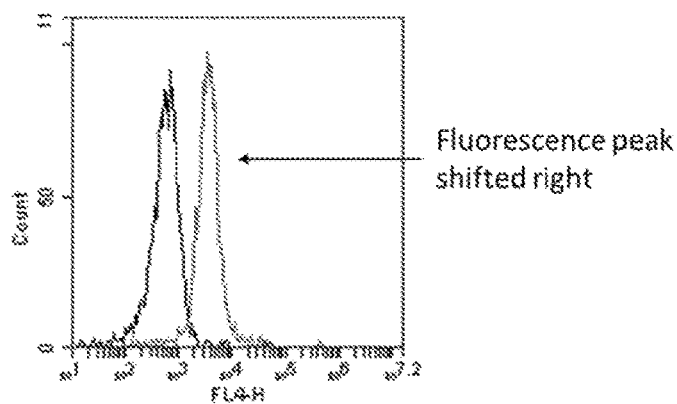

FIG. 13 illustrates Estimation of magnetic bead conjugation efficiency by flow cytometry.

Figure 14:
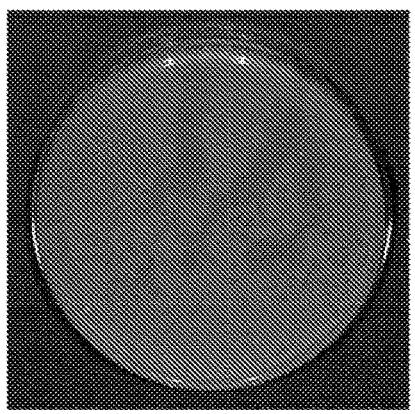
Figure 14:
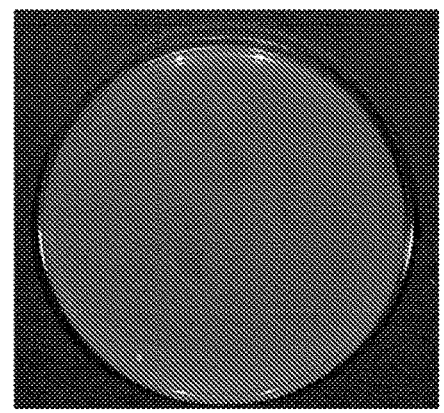

FIG. 14 illustrates Plaque assay of Antibody gene library after one round of panning.

Figure 15:
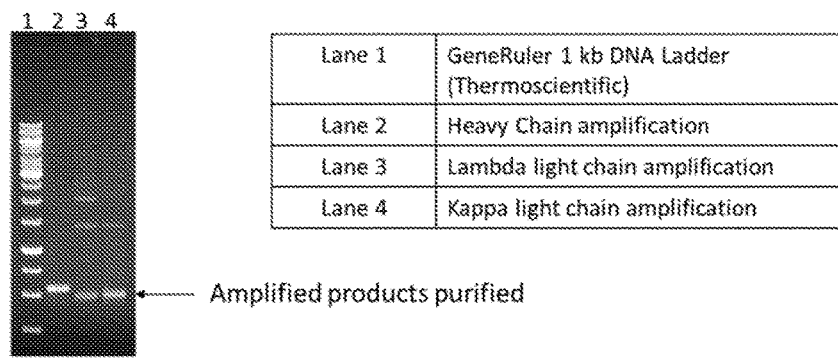

FIG. 15 illustrates PCR amplification of antibody heavy chain, antibody kappa chain and antibody lambda light chains from phage DNA.

Figure 16:
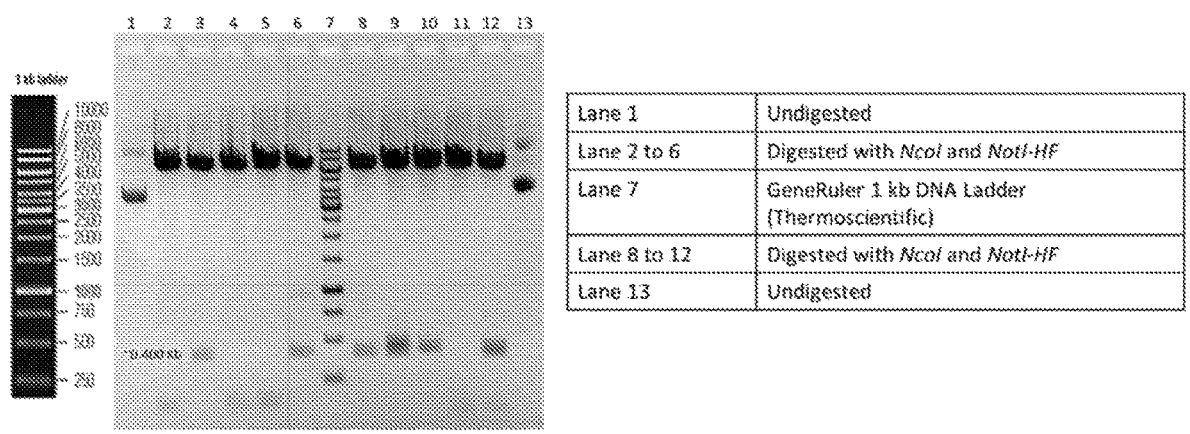

FIG. 16 illustrates Restriction enzyme digestion of Antibody heavy chain fragments after cloning to yeast expression system.

Figure 17:
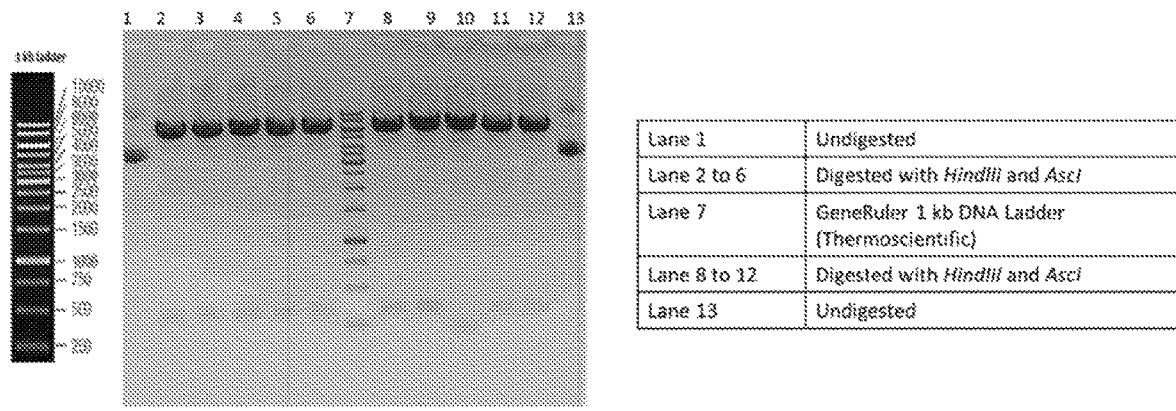

FIG. 17 illustrates Restriction enzyme digestion of Antibody light chain fragments after cloning to yeast expression system.

Figure 18:
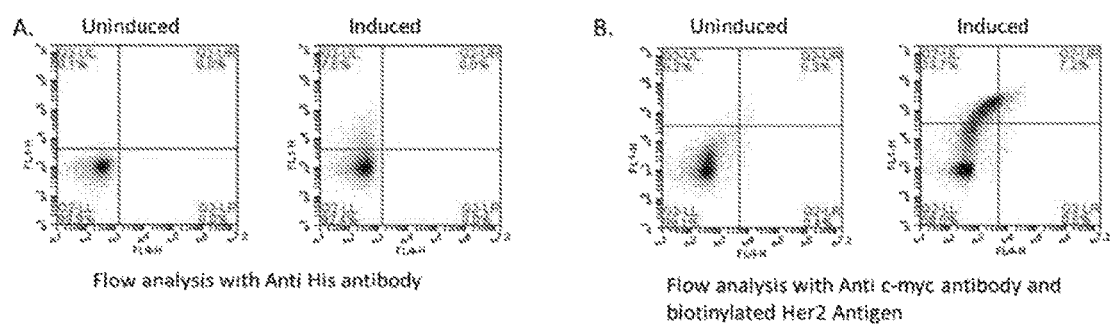

FIG. 18 illustrates Flow cytometry analysis to confirm antibody Fab expression.

Figure 19:
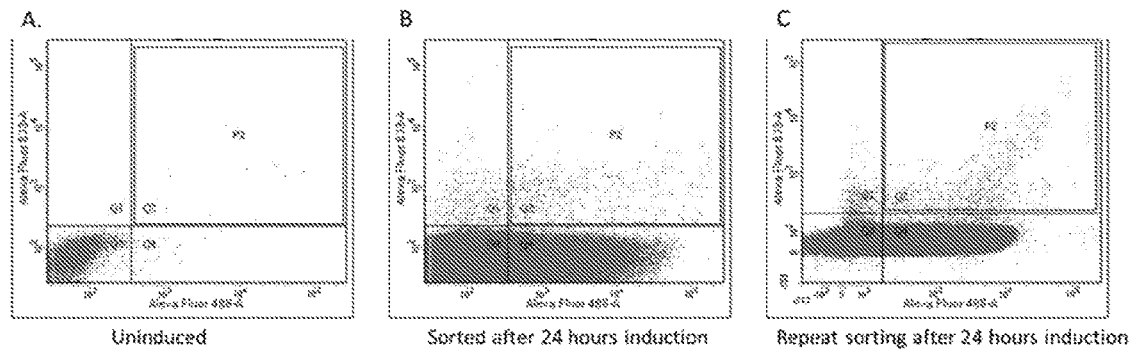
Figure 20:
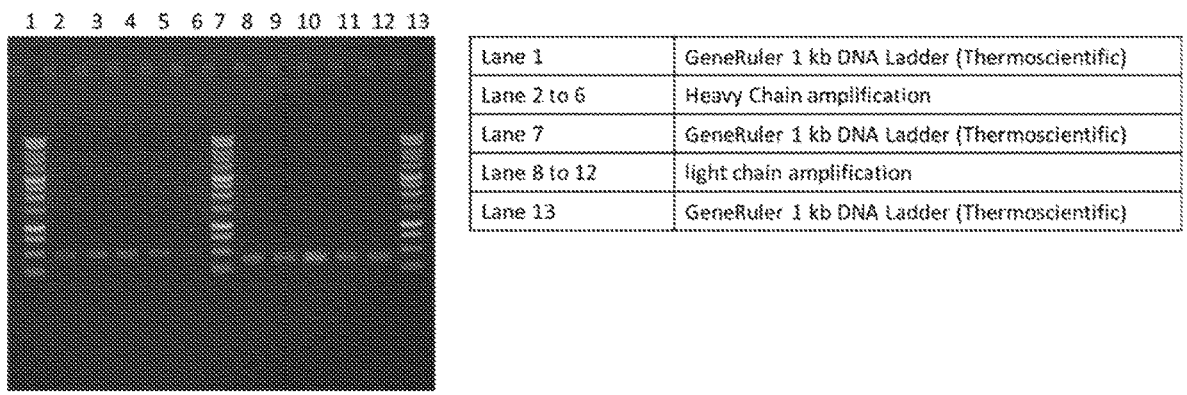
Figure 21:
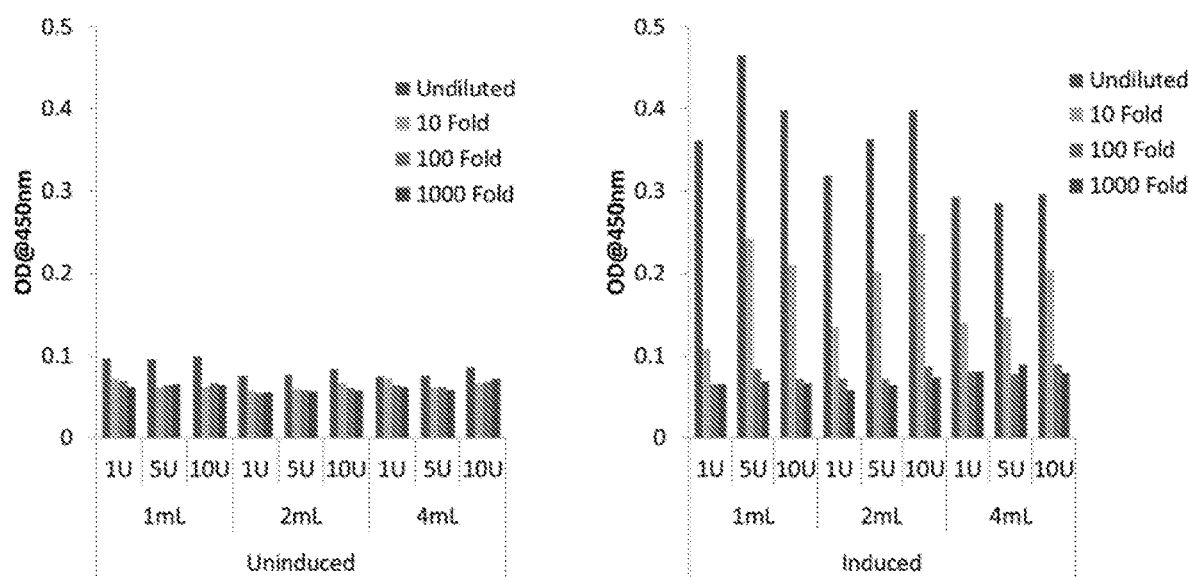

FIG. 19 illustrates Yeast surface display—Flow sorting of yeast cells expressing anti Her2 Fab. (A) Uninduced yeast cells showing no Fab expression, (B) Yeast cells induced for 24 hours showing Anti Her2 Fab, (C) Yeast cells are collected after initial sorting, further grown and flow sorting is repeated after 24 hours of induction FIG. 20 illustrates PCR amplification of heavy chain and light chain from diploid yeast cells after flow cytometric sorting FIG. 21 illustrates Yeast surface displayed antibody which is isolated using TEV protease cleavage and used in ELISA with Her 2 antigen. Left panel indicates uninduced yeast cells and right panel indicates induced yeast cells. TEV protease is used at 1 U to 10 U concentrations in corresponding culture volume of 1 mL, 2 mL and 4 mL. After TEV digestion the antibody containing mix is diluted and ELISA is carried out. Data represents undiluted samples to 1000 folds diluted samples.

Figure 22:
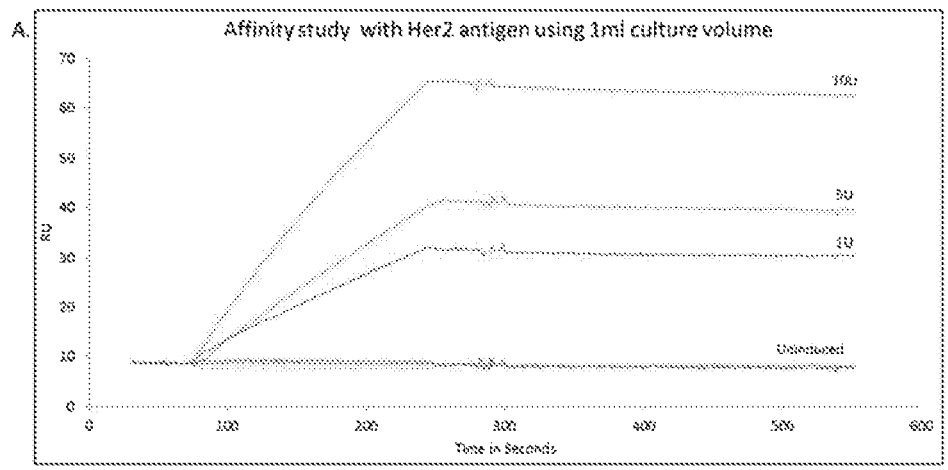
Figure 22:
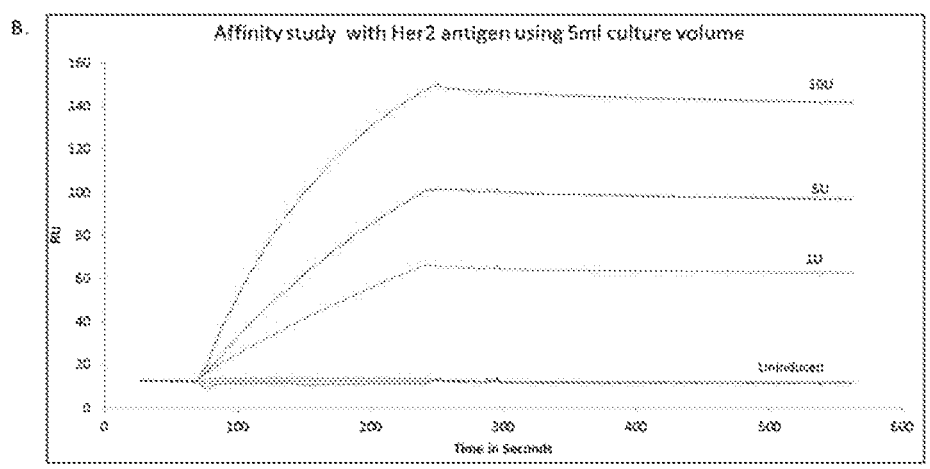

FIG. 22 illustrates Yeast surface displayed antibody which is isolated using TEV protease cleavage and used in BIACORE affinity study with Her 2 antigen. TEV protease is used at 1 U to 10 U concentrations in corresponding culture volume of 1 mL and 5 mL.

Figure 23:
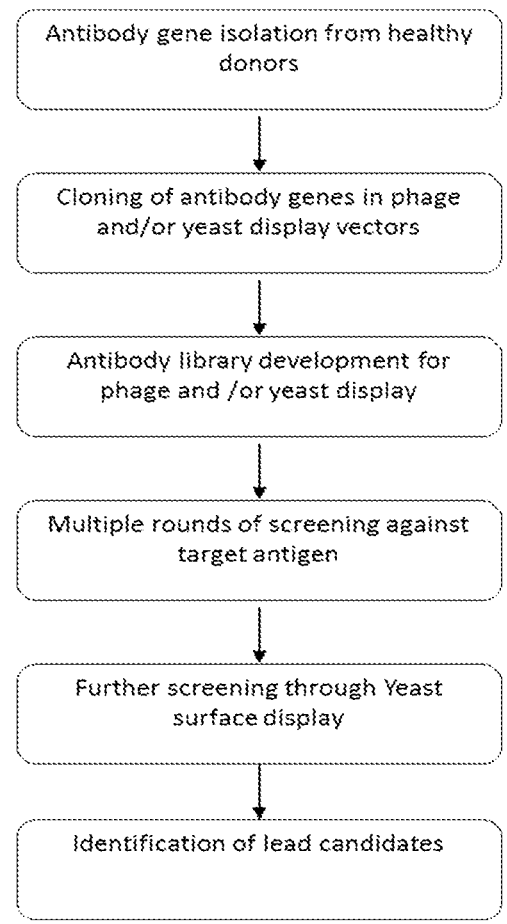

FIG. 23 illustrates a flow chart of the method of the human naive antibody library of the present disclosure.

Figure 24:
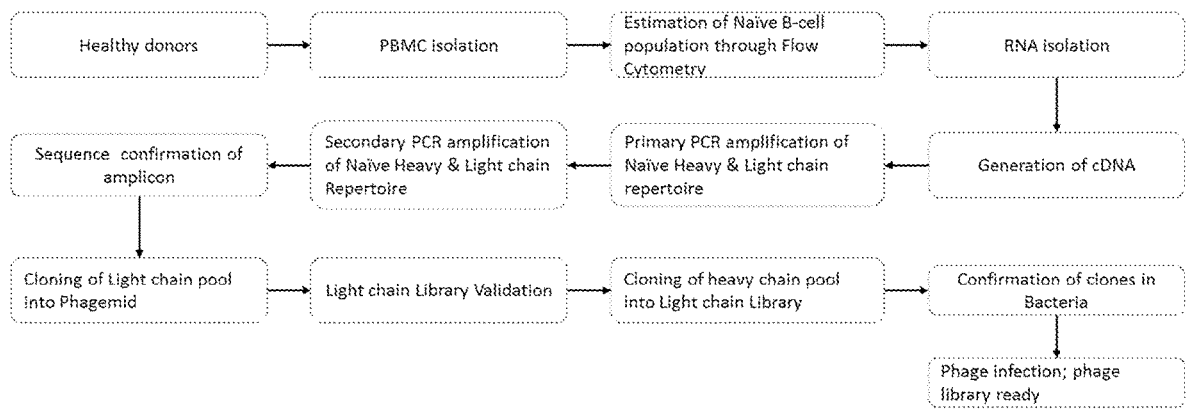

FIG. 24 illustrates a flow chart of Stage 1 of the process steps starting with blood sample collection to creation of antibody library in phage.

Figure 25:
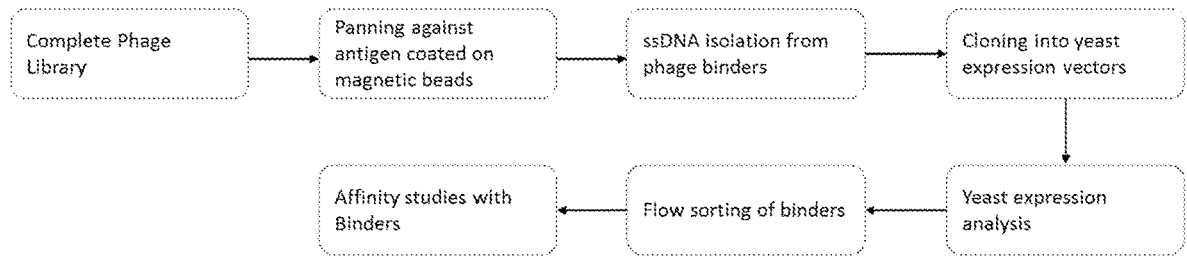

FIG. 25 illustrates a flow chart of Stage 2 of the process steps involving phage library screening to Yeast clone development using flow sorting of independent binders.

DETAILED DESCRIPTION OF THE DISCLOSURE

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular as is considered appropriate to the context and/or application. The various singular/plural permutations may be expressly set forth herein for the sake of clarity. Generally, nomenclatures used in connection with, and techniques of biotechnology, immunology, molecular and cellular biology, recombinant DNA technology described herein are those well-known and commonly used in the art. Certain references and other documents cited herein are expressly incorporated herein by reference. In case of conflict, the present specification, including definitions, will control. The materials, methods, figures and examples are illustrative only and not intended to be limiting.

Furthermore, the methods, preparation and use of the antibody naïve library disclosed employ, unless otherwise indicated, conventional techniques in molecular biology, biochemistry, computational chemistry, cell culture, recombinant DNA technology, Polymerase Chain Reaction (PCR) and related fields. These techniques, their principles, and requirements are explained in the literature and known to a person skilled in the art.

Before the method of generating the antibody naïve library and the nucleic acids which make up the antibody naïve library and other embodiments of the present disclosure are disclosed and described, it is to be understood that the terminologies used herein are for the purpose of describing particular embodiments only and are not intended to be limiting. It must be noted that, as used in the specification and the appended claims, the singular forms "a," "an" and "the" include plural referents unless the context clearly dictates otherwise.

As used herein, the terms "library" and "libraries" are used interchangeably within this disclosure which relate to the product of the disclosure. Furthermore, it refers to a collection or pool of nucleic acid sequences.

As used herein, the terms 'pooling', 'pooled', 'pool', 'pools' in the context of the instant disclosure means combining the samples/nucleic acid sequences/nucleic acid fragments/gene clones/amplified product/antibodies obtained by employing the method of the instant disclosure from multiple donors i.e., more than one donor.

As used herein, the term "PBMC" refers to any peripheral blood cell having a round nucleus consisting of lymphocytes (T cells, B cells, NK cells) and monocytes, erythrocytes, platelet, and granulocytes (neutrophils, basophils, and eosinophils).

As used herein, the term "Genetic Diversity" means total number of genetic characteristics for a population with variations of alleles.

As used herein, the term "ethnicity" means an inherited status for a population based on the similarities seen in a society the person lives.

As used herein, the term "Antigen" refers to any foreign substance which induces an immune response in the body.

As used herein, the term "antibody" refers to an immunoglobulin which may be derived from natural sources or synthetically produced, in whole or in part. The terms "antibody" and "immunoglobulin" are used synonymously throughout the specification unless indicated otherwise.

As used herein, the term "antibody" includes both polyclonal and monoclonal antibody preparations and also includes the following: Chimeric antibody molecules, F(ab')2 and F(ab) fragments, Fv molecules, single chain Fv molecules (ScFv), dimeric and trimeric antibody fragments, minibodies, humanized monoclonal antibody molecules, human antibodies, fusion proteins comprising Fc region of antibody and any functional fragments arising out of these molecules, where derivative molecules retain immunological functionality of the parent antibody molecule.

As used herein, the term "monoclonal antibody" in the present disclosure, refers to an antibody composition having a homogeneous antibody population. The antibody is not limited to the species or source of the antibody or by the manner in which it is made. The term encompasses whole immunoglobulins as well as fragments such as Fab, F(ab')2, Fv, and other fragments, as well as chimeric and humanized homogeneous antibody populations that exhibit immunological binding properties of the parent monoclonal antibody molecule.

As used herein, "antibody fragment" is a portion of a whole antibody which retains the ability to exhibit antigen binding activity. The terms Fab or ScFv are used as antibody fragments with specific mention.

As used herein, "Antibody display library" refers to a platform(s) expressing antibodies on the surface of cell or cell-free suited for a screening methodology against target antigens. Herein, phage display library and yeast display library are used with accurate specification unless indicated otherwise.

As used herein, the term "naïve library" refers to a collection of nucleic acid sequences encoding a naturally occurring VH repertoire from a non-immunized source.

As used herein, the term "VH" refers to the single heavy chain variable domain of antibody of the type that can be found in mammals which are naturally devoid of light chains or parts of the same; Naive VH can be understood accordingly.

As used herein, the term "VL" refers to single light chain variable domain of the antibody; they are found in two types based on the constant domain sequence. Vk (with kappa constant region) and Vl (lambda constant region) are understood accordingly.

As used herein, the term "CDR" refers to complementary determining region of the antibody structure.

As used herein, the term "repertoire," means a collection, indicating genetic diversity.

As used herein, the term "framework region" is used herein to refer to the nucleic acid sequence regions of an antibody molecule that encode the structural elements of the molecule.

As used herein, the term "Aga2p" refers to a yeast protein used as an anchor protein displaying antibody of interest on the yeast surface.

As used herein, "B cell" refers to a type of white blood cell of the lymphocyte subtype which functions in the humoral immunity component of the adaptive immune system by secreting antibodies.

As used herein, "Naïve B cell" mentions to a specific sub type of B-cell that has not been exposed to an antigen.

As used herein, the term "DNA" means deoxyribonucleic acid carrying the genetic instructions for life.

As used herein, the term "RNA" refers to a ribonucleic acid implicated in various biological roles such as coding, decoding, regulation, and expression of genes.

As used herein, the term "mRNA" means a family of RNA molecules that convey genetic information from DNA to the ribosome for translation.

As used herein, the term "cDNA" refers to a double-stranded DNA synthesized from a single stranded RNA (e.g., messenger RNA (mRNA) or microRNA (microRNA)) template in a reaction catalysed by the enzyme reverse transcriptase.

As used herein, the abbreviation "GAPDH" means Glyceraldehyde 3-phosphate dehydrogenase which is involved in glycolysis and known as housekeeping gene which is why it is often used as internal control in experiments.

As used herein, the term "reverse transcriptase" refers to an enzyme linked with retroviruses and used for generating complementary DNA (cDNA) from an RNA template, a process termed reverse transcription.

As used herein, the term "Immunoglobulin" refers to glycoprotein molecules acting as a critical part of the immune response by specifically recognizing and binding to particular antigens.

As used herein, the term "PCR" refers to polymerase chain reaction, a molecular biology technique that is used to amplify a segment of DNA using appropriate primers.

As used herein, the term "Primer" refers to a short fragment of DNA or RNA to initiate DNA synthesis.

As used herein, "Degenerate primer" refers to a mix of oligonucleotide sequences in which some positions contain a number of possible bases, giving a population of primers with similar sequences covering all possible nucleotide combinations for a given protein/antibody sequence. More specifically, the primers employed in the instant disclosure are set forth in tables 4 and 5 and unique primer sequences synthetically generated are captured in the Sequence listing section indicated as separate sequence ID's from SEQ ID 1 to SEQ ID 68. Said sequences incorporate a unique trinucleotide sequence therein. As said primer sequences are synthetically generated and not complementary to the native gene sequences occurring in nature, they are also referred as artificial sequences.

As used herein "vector" refers to a DNA related to a cloning or expression system to accommodate antibody genes in specific designated restriction sites. Phagemid vectors (applicable to phage display system) or yeast vectors (applicable to yeast display system) are understood accordingly.

As used herein, the term "Phagemid" refers to a DNA expression system wherein it can be replicated as a plasmid, and also be packaged as single stranded DNA in viral particles. Phagemid is used to accommodate the whole repertoire of antibody genes wherein post infection to bacteria it requires additional proteins provided by helper phage to create phage particles that display recombinant protein.

As used herein, the term "Phage" means a virus particle which infect bacteria and amplify.

As used herein, "Helper Phage" refers to a specific phage particle which supply all required proteins/materials to produce functional phage particles.

As used herein, the term "Plaque" refers to visible structure formed on lawn of bacteria due to cell destructions.

As used herein, "Phage amplification" refers to growth of phage particles.

As used herein, the term "Panning" refers to an affinity selection technique which selects for binders against a specific target/antigen.

As used herein "Salmon sperm DNA" refers to a low molecular weight deoxyribonucleic acid isolated from salmon sperm aiding phage DNA precipitation.

As used herein "ssDNA" refers to single stranded DNA.

The present disclosure relates to a method of generating antibody naïve library comprising
  processing biological sample(s) to isolate nucleic acid(s) followed by amplification,
  pooling of the amplified product(s) and cloning of antibody genes into phage to obtain phage antibody library followed by screening of displayed genes against antigen(s) to obtain panned phage antibody library or pooling of the amplified product(s) and cloning of antibody genes directly into yeast to obtain yeast antibody library displaying the antibody genes on surface of the yeast; followed by screening the displayed genes against antigen(s) to obtain screened yeast antibody library,
  transferring the panned phage antibody library of the phage library into yeast for display of said antibody genes on surface of yeast followed by screening the yeast displayed antibody genes against antigen(s) to obtain yeast screened antibody library, and
  selecting the phage or the yeast displayed antibodies/ genes with desired functional properties which form the naïve antibody library or isolating selected antibodies with desired functional properties from the phage antibody library or the yeast antibody library to generate screened antibody naïve library.

In an embodiment, the biological sample is selected from a group comprising blood or any sample expressing antibody genes In another embodiment, the biological sample is obtained from selected healthy donors or subjects, wherein the selection criteria is based on diversity in language spoken, ethnicity or geographical location of said donors or subjects; and wherein the subjects are human.

In yet another embodiment, the processing of biological sample involves isolating peripheral blood mononuclear cells selected from a group comprising lymphocytes, monocytes, platelets and granulocytes or any combination thereof from the blood sample followed by estimating naïve B-cell population therein through flow-cytometry.

In still another embodiment, the estimation of naïve B-cell population is carried out by identifying differential expression of cell surface or intracellular markers selected from a group comprising IgD, CD20, CD19, CD27, CD24 and CD38 or any combination thereof; and wherein the naïve B-cell population of about 10% to about 15% of total PBMC is obtained.

In still another embodiment, the isolation of nucleic acid(s) include isolating of m-RNA, followed by c-DNA generation.

In still another embodiment, the amplification involves primary PCR amplification followed by secondary PCR amplification by employing any of degenerate primers or combinations thereof set forth as SEQ ID no 1 to 68.

In still another embodiment, the PCR amplification is carried out for about 18 cycles to about 25 cycles, each cycle with denaturation step for about 1 min to about 2 min at about 94° C. followed by annealing step for about 1 min to about 2 min at about 50° C. and extension step for about 50 sec to about 90 sec at about 72° C.; and wherein the PCR products obtained post amplification are optionally purified.

In still another embodiment, the cloning into phage or directly into yeast involves antibody light chain cloning followed by antibody heavy chain cloning, both with transformation efficiency of about $10^8$ to $10^{10}$, preferably $10^8$; and wherein cloning into phage yields an estimated number of phage particles in the library in the range of $10^{10}$ to about $10^{11}$ pfu/mL.

In still another embodiment, the screening to obtain phage library involves panning with antigens coated on magnetic beads to isolate antibody of interest; and wherein said phage display screening/panning is employed to remove antibody non-binders.

In still another embodiment, the antibody format is selected from a group comprising Fab or ScFv.

In still another embodiment, the screening to obtain the yeast library by the surface display is carried out by employing competing antigenic epitopes, antibody paratope conformation, sequences and sequence motifs or any combination thereof to isolate Fab or ScFv molecule using protease cleavage sites selected from a group comprising Tobacco Etch Virus (TEV), Enterokinase, Thrombin, Factor X a, HRV 3C protease and similar protease cleavage proteins or any combination thereof.

In still another embodiment, the display of antibody library on surface of yeast involves isolation of plasmid DNA from phage library followed by restriction digestion, cloning and transforming in haploid yeast cells or in diploid yeast cells through mating of two haploid yeast cells.

In still another embodiment, the transferring is by transforming of the screened genes into yeast, with transformation efficiency of about $10^8$ to about $10^{10}$.

In still another embodiment, the yeast display screening is employed to execute affinity based selection, sorting of antibody binders.

In still another embodiment, the antibodies/genes are selected based on its binding with antigens by employing techniques/technologies selected from a group comprising flow cytometry, ELISA, bead based detection platforms, imaging and SPR or any combination thereof.

In still another embodiment, the naïve antibody library is a collection of the antibodies/gene expressed on surface of the phage or the yeast, or is a collection of the antibodies/genes isolated from the phage or the yeast or a combination thereof; and wherein the naïve antibody library comprises about $10^7$ to about $10^9$ clones.

The present disclosure also relates to a naïve antibody library obtained by the method as above.

The present disclosure also relates to Primer sequence(s) set forth as any of SEQ ID 1 to 68 wherein the primer sequence(s) is employed for obtaining the naïve antibody library as above or carrying out the method as above for generating/obtaining the naïve antibody library.

In an embodiment of the present disclosure, the sequence(s) encompass trinucleotide sequence tag(s) to catalogue antibody genes from respective geographical locations, which enables to trace the antibody genes back to original antibody gene pool.

The present disclosure also relates to a naïve antibody library as above or as obtained by method as above for use in therapeutics for treatment of diseases selected from a group comprising cancer, rheumatoid arthritis, neurological disorders, infectious diseases and metabolic disorders or any combination thereof; as diagnostics; as prognostics; for research purposes; target discovery; validation in functional genomics or any application where antibodies or derivatives of antibodies are employed.

The present disclosure relates to a method of generating an antibody library not limiting to a human naïve antibody gene expression library. Said human naïve antibody library comprises a pool of nucleic acid sequences derived from a natural antibody repertoire comprising humoral immunity from healthy and genetically diverse human populations.

In an exemplary embodiment, combinatorial tools including phage display technology and yeast display technology are employed in the present method for generating antibody library. In another embodiment, the method employs phage display technology sequentially followed by yeast display technology to create human naïve antibody gene expression library.

In a non-limiting embodiment of the present disclosure, the human naïve antibody gene expression library allow isolation of unique antibody molecules with the desired functional properties for a specific therapeutic target i.e., antigen. A human naïve antibody library in the present disclosure relates to a collection of pooled antibody nucleic acid sequences which are prepared by employing the method as detailed by the disclosure.

In a non-limiting embodiment of the present disclosure, the desired functional properties of the antibodies are selected from a group comprising, but not limiting to affinity, specificity, manufacturability, generation of new epitopes, thermal stability, antigenicity, solubility, aggregation and catalytic activity, or any combination thereof. Said functional properties are natural extensions or inherent properties of the naïve antibody library generated by employing the method of the present disclosure. Scope for further enhancing said properties exists.

In a non-limiting embodiment of the present disclosure, the method of generating the naïve antibody gene expression library includes identifying multiple healthy donors who are categorized based on genetically diverse profiles or inclusion/exclusion criteria, such as but not limiting to language, ethnic background, geographical location etc.

In another non-limiting embodiment of the present disclosure, the method of generating the human naïve antibody gene expression library, includes isolating antibody expression genes from biological samples such as blood samples of each individual donor to create a library of genes from diverse genetic makeup. Biological samples can also include spleen, bone marrow or any sample expressing antibody genes.

In an exemplary embodiment of the present disclosure, blood samples are collected from healthy blood donors who are identified based on inclusion/exclusion criteria following the prevailing ethical and regulatory norms.

In another non-limiting embodiment of the present disclosure, the method of generating the naïve antibody gene expression library, includes sequentially exploring the expression profiles of a pool of gene clones by utilizing two separate scanning tools, 1) a phage display technology and 2) a yeast display technology. Sequential use of these technologies allows in harnessing larger set of antibody gene diversity, a character of phage based library. The antibody clones are thereafter screened through yeast display system. Use of yeast system for antibody gene expression is advantageous because of eukaryotic protein translation, processing and proper folding of the antibody products on cell surface. Further, yeast expression allows proper interaction with antigenic targets with high specificity. Information obtained using these two complementary systems generates "lead molecules" (i.e., antibodies specific to an antigen) with higher success rate in terms of commercialization potential.

The expression profiling and screening strategies adopted in the present disclosure enables to smoothly transit between phage to yeast display platforms. The phage display accommodates the library size (~$10^{11}$) for primary screening which is focused on stringency and specificity of antibody-antigen interaction in a high-throughput format while screened molecules would again go through a randomization process to mimic native display via yeast platform. Thus, each platform contributes combinatorially to the pipeline of developing functionally specific yet structurally varied antibody moieties. The process of multiple rounds of selection on an antigen or on antigen-expressing cells via two different display systems are extremely valuable to positively or negatively select a range of desired antibody properties, such as but not limiting to affinity, specificity, manufacturability, new epitopes, thermal stability, antigenicity, solubility, aggregation of antibodies, catalytic activity etc. The present method enables to preserve diversity in the library that is capable of identifying unique molecules against varied antigenic targets. Generation of the naïve library of human antibodies with high diversity serves as a tremendous resource for new antibody identification and further commercial development.

In yet another non-limiting embodiment of the present disclosure, the methodology also involves a strategy wherein the diversity is translated between two platforms and explored as various engineered antibody formats such as, but not limiting to chimeric antibody molecules, Fab, fragments, F(ab')2 fragments, Fv molecules, ScFv, ScFab, dimeric and trimeric antibody fragments, minibodies, humanized monoclonal antibody molecules, human antibodies, fusion proteins comprising Fc region of antibody, any functional fragments arising out of these molecules where derivative molecules retain immunological functionality of the parent antibody molecule and all other antibody formats.

In an exemplary embodiment, the term "monoclonal antibody" in the present disclosure, refers to an antibody composition having a homogeneous antibody population. The antibody is not limited to the species or source of the antibody or by the manner in which it is made. The term encompasses whole immunoglobulins as well as fragments such as Fab, F(ab')2, Fv, and other fragments, as well as chimeric and humanized homogeneous antibody populations that exhibit immunological binding properties of the parent monoclonal antibody molecule.

In still another non-limiting embodiment, the candidate antibody molecules obtained by the present method are further optimized through rational designing guided by structure-function studies of antibody-antigen interactions. The process of drug development especially antibody based drugs, is challenging, time consuming, and expensive. Several multidisciplinary approaches are required to meet these challenges which collectively form the basis of rational drug designing. The prerequisite for success of manufacturability of monoclonal antibody drugs are dependent on a variety of biological and/or correlated properties such as solubility, aggregation, antigenicity, stability and so on. Many of these properties are dependent on different structural motifs of antibody; which could be predicted through in silico approaches. As exemplified, structure-based drug designing which is rational, evidence based and faster, has contributed tremendously in the field of cancer chemotherapy, drug resistant infections, neurological diseases, to mention a few. The resulting outcome of these methods is employed in the instant disclosure to improve antibody library construction and manufacturability of selected molecules.

In still another non-limiting embodiment, the method of the present disclosure also involves incorporating yeast mating type based strategies, a feature of the haploid/diploid lifecycle of yeast which allows generation of larger libraries (ScFv or Fab or full antibody) in yeast from two separate yeast vectors and is also amenable to chain randomization for affinity improvement.

Taken together, the method of the present disclosure is centralized around combinatorial library techniques aiming at more efficient generation/utilization of the antibody repertoire. Naïve antibody library allow in vitro selection of human mAbs of virtually any specificity and affinity. Owing to its design, this technique permits both genetic and functional analyses of the selected mAbs thus facilitating studies on mechanisms of the human immune system. Translational research approaches embracing such library may converge on new future therapies.

In a non-limiting embodiment of the present disclosure, the features such as larger library size and diversity in genetic make-up of donors are suspected to be directly linked to achieving improved antibody specificity and affinity.

In a non-limiting embodiment of the present disclosure, the antibody library such as naïve antibody library allows for isolation of unique antibody molecules with the desired functional properties for a specific therapeutic target i.e., antigen. Uniqueness of the said category of library is to have a wide variety of antibodies which are not deleted from immune system by tolerance mechanism and believed to cover any possible antigen.

The present method of generating or development of the human naïve antibody library is set forth in the flow chart in FIG. 23.

The humoral immune response recognizes novel molecular surfaces by exposure to a vast repertoire of potential binding partners i.e., antigens. In 1989, the first functional antibodies were isolated from a combinatorial antibody library derived from an immunized Mouse. Antibody paratopes, the agents of humoral molecular recognition, mediate specific binding through a protein-antigen interface that varies dramatically between molecules. Such library exhibits low affinity when confronted with a novel antigen. Therefore, the diversity of the antibody repertoire determines whether a specific complementary paratope will be recovered or not. Under such selective circumstances, a number of mechanisms to maximize the recognition potential of the antibody repertoire plays a crucial role in selecting its right partner. Antibody paratopes are found at the hypervariable region of a light and heavy chain heterodimer wherein each chain contributes three loops to a spatial distributed cluster of complementarity determining regions (CDRs). The natural primary (unselected against antigen) antibody repertoire within B cells contains a large array of antibodies that can potentially recognize a variety of antigens; this array can be tapped as a "naïve" or non-immune repertoire of rearranged genes, by harvesting the V-genes from the IgM mRNA of B cells of unimmunized human donors, isolated from peripheral blood lymphocytes. Moreover, the advantage of exclusively designed expression system, display platform along with combinatorial approach will provide access to large antibodies diversity that have not yet encountered antigen, although the frequency of those "germline" antibodies will depend heavily on the source of B cells.

The present method of generating human naïve antibody library and screening against antigen(s) comprises the acts/steps of:
  a) isolating PBMCs from blood of multiple donors;
  b) processing the PBMCs to obtain RNA (mRNA) followed by amplification; c) pooling the amplified product (antibodies genes) and cloning into phage and/or yeast vectors to generate naïve phage or yeast library followed by expression and screening said product against antigen(s);
  d) transferring/cloning screened product of step c) into yeast vectors followed by screening said product against antigen(s); and
  e) selecting antibodies with desired functional properties from phage and/or yeast libraries.

In a preferred embodiment of the present disclosure, the present method of generating the human naïve antibody library comprises the following steps wherein multiple healthy donor population are categorized based on genetically diverse profiles followed by isolating PBMCs from collected donor blood samples. Thereafter, the PBMCs are processed for RNA (mRNA) isolation followed by cDNA generation and amplifying the IgM pool of antibody chains by employing degenerate primers. The amplified nucleic acid fragments are pooled and cloned into phage and/or yeast vectors followed by carrying out about two to about five rounds of library screening against specific antigen targets. Thereafter, screened pool of molecules are cloned into yeast vectors and about one to about three rounds of screening against specific antigen targets is done. Specific populations showing higher affinity to target antigen or other desired antibody characteristic(s) are isolated, individual clones are separated and clonal populations obtained therefrom are used for selecting specific molecule for further antibody development.

In an exemplary embodiment of the present disclosure, the method of generating the human naïve antibody library comprises the following steps.

Step 1: identifying multiple healthy donors who are categorized based on genetically diverse profiles or inclusion/exclusion criteria including but not limiting to language, geographical location and ethnic background, and collecting blood samples from the donors followed by isolating PBMCs from the samples by employing process known as Ficoll-paque, hisPaque. The samples are identified/tested for presence of naïve B-cells by testing for specific markers. Source of nucleic acid pool i.e., IgM RNA for naïve library originates from naïve B-cell that are present in peripheral blood mono nuclear cells (PBMC) fraction of blood samples. Step 2: isolated PBMCs are processed for mRNA isolation and further converted to cDNA in vitro. Step 3: unique set of degenerate primers are used to amplify naïve IgM pool of antibody chains. The unique design of primers also includes a specific trinucleotide marker which is specific to each group of donors. Later on, these markers are used to trace library screened molecules back to its original population, if required. Step 4: Amplified naïve pool of nucleic acid fragments (via primary and secondary PCR) from different groups are pooled together purified, checked for functional diversity and cloned in specific set of phagemid (preferably in-house phagemid) and/or yeast vectors with a notion of capturing the vast size and diversity of the library molecules. Step 5: The screening of library of molecules is done by bio-panning via multiple rounds of selection against specific antigen. During each round, specific binders are selected out from the library by washing away non-binders, Step 6: Selected pool of molecules screened in phage display platform is transferred with or without randomization of selected diversity to a eukaryotic system i.e., yeast display platform avoiding any PCR based method, thereby, preserving the selected pool of molecules. This transfer is specifically done to overcome issues with folding and pairing of heavy and light chains in phage display platform. Yeast display platform comprises of various set up expressing variety of antibody moieties in different formats. Step 7: Displayed fragments are screened against specific antigenic targets and specific populations showing higher affinity to the target antigen are separated. Step 8: These selected pools are further tested for antigen specificity, if required. Step 9: Finally, individual clones from the selected pools are separated and clonal populations are used for isolating nucleic acid sequences coding for the "lead molecules". Careful analyses and understanding of antibody-antigen interaction studies using several bio-informatics tools will allow further incorporation of changes in nucleic acid sequence of the lead molecules. The screening system is integrated with antibody characteristic such as but not limited to affinity, new epitope, thermal stability, aggregation, solubility, antigenicity and other properties related to successful antibody product commercialization.

Sequential use of phage and yeast display platforms expressing human naïve antibody repertoire, which are developed via combinatorial approach, permit to screen a wide range of therapeutic targets and steer to identification of unique antibody molecules with unique affinity. Flexibility of combinatorial yeast display system/platform and phage display system is not only for the various output formats such as Fab, ScFv, molecules or any antibody format, but it is also a convenient choice for haploid cell expression and diploid cell expression. Multiple option availability enables this combinatorial yeast display and phage display format a unique, flexible and indispensable platform to select ligand mimicking the in vivo immunoglobulin structure, a success. Detailed understanding of these target molecules would be a starting point to modify these at the level of nucleic acid incorporating the knowledge of antigen-antibody structure-function studies and scope of generating a lead molecule with increased affinity, stability, expression, efficacy etc. Hence, the present disclosure archives not only unique monoclonal antibodies identification against targets of various diseases not limiting to cancer, rheumatoid arthritis, neurological disorders, infectious diseases and metabolic disorders; but also to play a vital role in target discovery and validation in the area of functional genomics.

The present disclosure also relates to an antibody gene expression library comprising a repertoire of naïve nucleic acid sequences prepared from wide and genetically diverse populations by employing the method of the instant disclosure.

The present disclosure also relates to an antibody library obtained by employing the method of the present disclosure, wherein said library can be developed and improved further by adding additional sets of healthy blood donors, antibody gene sequences of various groups and/or individuals etc., by employing antibody rational designing. Such an iterative approach increases the possibilities of enriching/adding to the pool of exclusive antibody molecules in the library.

The present disclosure also relates to use of an antibody gene expression library comprising a repertoire of naïve nucleic acid sequences prepared by the method of the present disclosure, to screen against antigen targets.

In a non-limiting embodiment, the antibody gene expression library of the instant disclosure finds application in several fields, including, but not limiting to therapeutics, diagnostics, prognostics, research purposes and virtually any application where antibodies or derivatives of antibodies are employed.

Antibody display library represents a library of partial or complete antibodies expressed on cell surface linked to other cellular proteins. Phage display is the most accepted method due to ease of cloning, allowing for large library sizes, monovalent display and easy to determine various stability parameters. However, with phage display there are associated limitations on proper protein folding due to prokaryotic expression system and lack of post translational modifications of the displayed antibody fragments thereby. To overcome these limitations, yeast display platform, a robust, versatile, quantitative methodology for isolating and engineering antibody fragments is employed. Yeast, a eukaryotic display system is of choice as it is compatible with quantitative and real-time assessment employing fluorescence activated cell sorter (FACS)-sorting techniques.

In comparison with other in vitro display technologies, yeast display of naïve/non-immune antibody libraries using the agglutinin adhesion receptor complex Aga1 and Aga2 has a significant number of advantages. For example, use of flow cytometry analysis allows rapid clone characterization including KD determination, koff measurement and epitope binding of mutually exclusive clones directly on the surface of yeast. This eliminates the need for purification of protein to perform these characterizations. The successful display of Fab antibody fragments on yeast suggests a simpler approach to large library construction. As Fab fragments are composed of heavy and light chains, therefore it is possible to encode the two polypeptides on different vectors in different yeast strains wherein two chains can be brought together in a single diploid yeast by mating, a highly efficient process. However, major challenge in case of yeast display is relatively smaller library size due to lower transformation efficiency in yeast, which is hereby overcome by the aspects provided by the instant disclosure, which employs a combination of phage and/or yeast display concept.

The present disclosure is further described with reference to the following examples, which are only illustrative in nature and should not be construed to limit the scope of the present disclosure in any manner.

EXAMPLES

Materials Employed:
SepMate™ tube (Stem cell technologies, Canada); Histopaque (SIGMA, St. Louis, USA); DPBS (GIBCO, USA); FBS (Moregate Biotech, Australia); FITC Mouse anti human IgD (BD Biosciences, USA); PE mouse anti human CD20 (BD Biosciences, USA); perCP-Cy5.5 mouse anti-human CD19 (BD Biosciences, USA); APC mouse anti-human CD27 (BD Biosciences, USA); PE mouse anti-human CD24 (BD Biosciences, USA); APC mouse anti-human CD38 (BD Biosciences, USA); Qiagen RNeasy Mini kit (Qiagen, USA); dNTPs (Ambion, USA); Superscript IV; random Hexamer, oligo d(T)16 primer (Invitrogen, USA); dNTPS (Ambion, USA); 1 Kb Ladder (Invitrogen, USA); Phusion enzyme (NEB, USA); Agarose (SIGMA, USA); PCR purification Kit (Qiagen, USA); Agarose (SIGMA, USA); Gel elution Kit (Qiagen, USA); pTZ-57R/T (Thermo Scientific, USA); Mini prep Kit (Qiagen, USA); Taq Polymerase (NEB, USA); dATP (NEB, USA); T4 DNA ligase (NEB, USA); LB-Agar (Himedia, India), Neb5alpha (NEB, USA); Ampicillin (MP Biomedicals, USA); NcoI-HF, (NEB, USA); XbaI, (NEB, USA); HindIII-HF, (NEB, USA); AscI (NEB, USA); HindIII-HF, (NEB, USA); AscI (NEB, USA); NotI (NEB, USA), TG1 cells (Lucigen, USA); T4 DNA ligase (NEB, USA); PCR purification Kit (Qiagen, USA); LB-Agar (Himedia, India); Mini prep Kit (Qiagen, USA); LB-Broth (Himedia, India); Ampicillin (MP Biomedicals, USA); Kanamycin (MP biomedicals, USA); M13KO7 helper Phage (Thermo Scientific, USA); Glycerol (Fischer Scientific, USA); PEG 8000, (SIGMA, USA); Sodium Chloride, (SIGMA, USA); TEV Enzyme (Invitrogen, USA); PBS (SIGMA, USA); BSA (Biovision, USA); Anti-FLAg, (Sigma, USA); HRP Goat Anti-mouse (Biolegend, USA); TMB Substrate (Sunmodics, USA); Herclon® (Roche, USA); Goat-Anti human IgGFc-HRP Conjugated (Bethyl, USA); Tween 20 (Fisher Scientific, USA); Her2 (Acrobiosystems, China);

Example 1

Generalized Procedure for Naïve Antibody Library Generation.

The success of naïve libraries solely depends on the final library size which should be sufficiently large. Naïve antibody library size & diversity and antibody specificity & affinity are directly linked. Healthy blood donor selection process is randomized in terms of selection of individuals from either sex. All individuals are screened for regular blood testing as is done for blood donation for transfusion purposes. Individual donor is categorized based on factors not limiting to geographical location, language (mother tongue) and ethnic background. Based on this information the collected samples are classified in multiple groups.

Blood samples are collected from multiple healthy donors of diverse language and ethnic background. Peripheral blood mononuclear cells (PMBCs) are isolated and processed for Ig-m-RNA isolation which is then converted to cDNA (in vitro). Said cDNA pool is further used for capturing naïve antibody gene repertoire. Specific tri-nucleotide marker containing degenerate primers is used to amplify the IgM pool and amplified fragments are pooled and cloned into a unique phagemid, developed in-house. The broad classification of PBMC samples will be tagged with specific trinucleotide sequence for tracing back antibody clones to particular population. Phagemid pool of naïve library is panned for multiple rounds against specific antigen solely based on stringency followed by confirmation using ELISA based method. Selected pool of molecules are transferred to specific yeast display vectors avoiding any PCR-based technology thus preserving the diversity. However, a randomization of heavy and light chains is allowed to compensate the differences across two display systems. The displayed fragments are screened against specific antigenic targets and the populations showing higher affinity to target antigens are separated. Selected pools are optionally tested for antigen specificity and individual clones from the pools are separated and clonal populations are used for isolating nucleic acid sequences coding for the lead molecules.

Example 2

To obtain sufficient number of naive B-cells in PBMC, blood samples are collected from multiple healthy donors. The donors are strategically chosen from various geographical locations in India with a specific language spoken. The confirmation of naïve B-cell population is necessary not only in terms of confirmation of surface markers in PBMCs but also in terms of the number which should be sufficiently large to tap all possible theoretical diversity present in Naïve B-cell population. The number of Naïve B-cells is never less than $10^7$. To avoid any kind of instability and related issue with isolated RNA, the PBMC samples are processed for RNA isolation and cDNA generation on the same day. The quantity of isolated RNA, that is used to generate cDNA, is ~10-25 μg from each region, sufficiently large enough and covering the theoretical antibody diversity number. Setting up PCR reaction with ~100 various degenerate primers with limited number cycles 10-18 is performed to ensure complete tapping of repertoire while there is less probability of PCR-mediated incorporation of mutation. The same is retained for secondary PCR as well. Moreover, the primary PCR amplicon amount is kept 50-150 ng per reaction to make sure that numbers of amplicon molecules are not limited. The trinucleotide marker is strategically placed in order to screen the region specific library later on. Cloning of light chain and heavy chain repertoire is carried out in Fab format with a mandatory transformation efficiency of $>10^8$ wherein the confirmation of presence of insert is done by restriction digestion analysis and which is not less than 90-95%. Optionally, peer group sequencing is further executed to estimate the functional diversity, which is expected to be >80%. Phage library generation is carefully carried out with correct number of phage particles which is $10^{10}$-$10^{11}$. For panning experiments against antigens, the magnetic based approach is adopted in order to have a better control on the binders. For the preparation of antigen coated on magnetic dynabeads the bead conjugation efficiency is set at >90%. Moreover, the panning is fixed at one round to remove only non-binders with a number not more than $10^7$ phage particles. This step is well aligned with the next step of yeast display library screening. In order to avoid any biased amplification or target unrelated population enrichment, a fixed 90 minutes of phage amplification duration is employed. To transfer the panned naïve library, ssDNA is isolated in the presence of salmon sperm DNA followed by amplification of insert ie., heavy and light chain repertoire. Purified repertoire is digested and ligated into yeast expression vectors in either fab format which are bi-directional, uni-directional or mating type vectors or ScFv format which is ScFv vectors. In all cases the transformation efficiency in yeast is $>10^7$. Transformed yeast cells are checked for heavy chain, light chain and Fab molecule expression which is not less than 15-50% of the whole population. For mating type the mating efficiency is ranging from 30-50%. The expression analysis is performed with multiple tags such as FLAG, c-Myc and His-tag and V5-tag for heavy chains and light chains respectively. Flow based sorting for antigen binding is analysed with double positive for both antigen and either of the heavy or light chain. Sorted molecules are re-sorted at least once more before they were grown individually and tested for binding studies. Both ELISA and SPR based studies are performed to confirm and re-confirm the antigen binding with Fab/ScFv molecules.

The flow charts in FIGS. 24 and 25 describe the important process steps of the present disclosure.

The flow chart in FIG. 24 describes Stage 1 process steps starting with blood sample collection to creation of antibody library in phage.

The flow chart in FIG. 25 describes Stage 2 process steps involving phage library screening to Yeast clone development using flow sorting of independent binders Example 3

Figure 1:
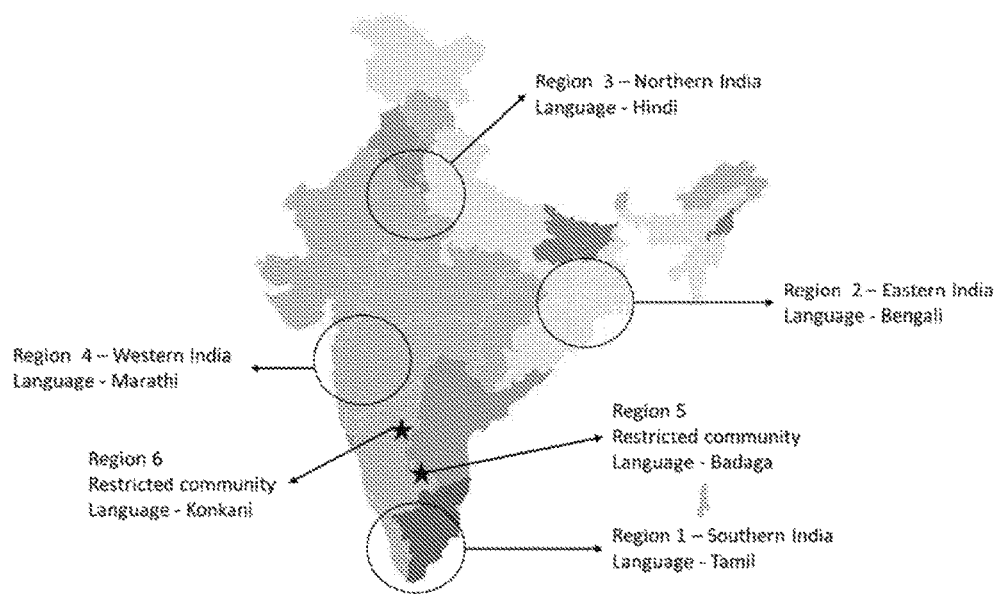
FIG. 1 illustrates Regions of sample collection: Geographical locations and languages spoken are shown.

Selection of PBMC Donor:

The study participants are selected from independent healthy blood donors of either sex from various regions in India (FIG. 1). All individuals are screened for regular blood testing as is done for blood donation for transfusion purposes. Individual donors are categorized based on few important criteria including unique language spoken (mother tongue), ethnicity and specific geographical location. All voluntary donors are informed and provided informed consent following regulatory processes.

Collection of Sample:

Biological sample such as blood samples are successfully collected at a volume ranging from 200-250 mL. Blood samples are collected from genetically diverse volunteers from five or more unique and distinct regions in India. Samples are coded appropriately at the source to maintain anonymity. Existing guidelines such as diet resume, volume of blood to be collected are strictly followed for each volunteer. Blood collection is performed from each volunteer in accordance with a medical science approved procedure. The blood report is carefully looked in to by medical practitioners prior to any further processing.

Isolation of PBMC:

The adopted method for separation and isolation of PBMC for all samples is a process known as Ficoll-paque, histoPaque (SIGMA). This density gradient medium is performed using SepMate™ tube based on the principle of differential migration of blood cells through the media during the centrifugation stage of the procedure. The blood sample is mixed with 150 mL DPBS buffer containing of 2% FBS. Further, 15 mL of histopaque is added into the Sep-Mate tube followed by addition of 30 mL of PBMC buffer mixture into it. The whole mixture is spun down at 1200 g for 10 minutes. The PBMC layer is collected and diluted with 50 mL of DPBS buffer containing 2% FBS followed by centrifugation at 300×g for 10 min. The supernatant is discarded while the pellet containing the pure PBMC is re-suspended in 2 mL of DPBS buffer containing of 2% FBS. The anticoagulant or defibrinated blood specimens are carefully layered on top of the Ficoll solution, followed by centrifugation to form different layers containing different types of cells. The bottom layer consists of red blood cells (erythrocytes) and granulocytes which are collected or aggregated by the Ficoll medium. The top layer consisting PBMC(s), is typically at the interface between the plasma and the Ficoll solution. To recover the PBMC, this layer is carefully recovered, washed with a 2% FBS containing buffer through centrifugation. The use of isolated PBMC from blood samples for the amplification of antibody gene fragments to develop antibody display libraries is approved by ethical committee.

Figure 2:
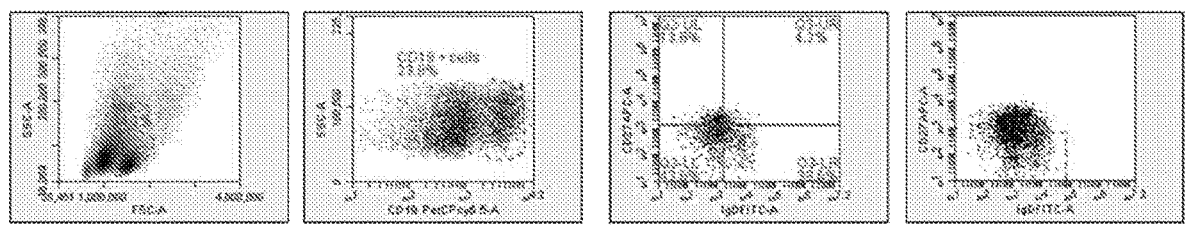
FIG. 2 illustrates Analysis of PBMC using flow cytometer.

Identification of Naïve B-Cell Population/Naïve B-Cell Estimation:

Differential expression of cell surface and intracellular markers, as well as their distinct immunoglobulin and cytokine secretion profiles, provide valuable clues to the diverse nature and function of the different B-cell subsets. Presence or absence of various unique markers (Eg: IgD, CD20, CD19, CD27, CD24, CD38) is exploited to identify specific sub-set of B-cell population. Isolated PBMC samples from each volunteer is tested for microscopic validation for RBC contamination and found to be RBC free. Further, to have an estimate of number of total PBMC and number of Naïve B-cell in it, flow cytometry based experiments are performed, wherein use of comprehensive selection of antibodies that is CD19+/CD27+/IgD-cell population in PBMC is considered as Naïve B-cell population (FIG. 2). $1 \times 10^6$ cells are taken and re-suspended in 1×PBS containing 1% BSA followed by incubation with antibodies for 25 minutes on ice (See Table-1). Post incubation the samples are centrifuged for 5 minutes at 1500 rpm followed by re-suspension in 1×PBS containing 1% BSA. The suspension is centrifuged at 2500 rpm for 5 minutes followed by addition of 1×PBS with 1% BSA. The samples are run through flow cytometric analysis. The other set of markers are also trapped to differentiate from non-B lymphocytes and other B-cell subsets such as transitional B-cell, memory B-cells etc. Approximately, 40 to 50 million PBMC cells are isolated from each sample. Estimated naïve B-cell population is ranging from 4 to 5 million per sample. Considering five regions together, a total number of ~$10^7$ cells are used to tap the naïve antibody repertoire. Considering the number of theoretical diversity for heavy chain and light chain repertoire, the available numbers of Naïve B cell is large enough to tap all possible diversity.

TABLE 1

|  | Tube 1 (unstained) | Tube 2 | Tube 3 | Tube 4 |
|---|---|---|---|---|
| Ig-D | — | 20 uL | — | — |
| CD 20 | — | 10 uL | — | 10 uL |
| CD 19 | — | 5 uL | 5 uL | 5 uL |
| CD 27 | — | 10 uL | — | — |
| CD 24 | — | — | 20 uL | — |
| CD 38 | — | — | 10 uL | — |

Total RNA Isolation:

In order to prevent any storage related issues which might interfere with the RNA yield or quality, the total RNA isolation is completed on the same day of sample isolation with utmost care. Approximately $10^7$ numbers of cells are re-suspended in 650 μL of RLT buffer followed by transferring suspension including any precipitate, to an RNeasy Mini spin column placed in a 2 ml collection tube and centrifuged for 15 s at ≥8000 g. The flow-through is discarded and the column is washed with 700 μL of RWT buffer at ≥8000 g for 20 s. The column is washed and centrifuged twice with 500 μL of RPE buffer for 15 s and 2 min, respectively at ≥8000 g. The RNA is eluted in 30 μL of nuclease-free water by centrifuging for 1 min at ≥8000 g. Sample from each region yielded total RNA ranging from 15-20 μg. Further analysis of RNA sample indicated a high purity of each RNA sample that is directly used for cDNA generation.

cDNA Generation:

In order to completely recover the entire antibody gene repertoire, cDNA is prepared with both random hexamer and Oligo dT as primers; ~0.6-1 μg of total RNA for each primer with Superscript™ IV is used for the first-strand cDNA synthesis. RNA-primer (random primer or Oligo dT) and 1 μL of 10 mM dNTP mix mixture are incubated at 65° C. for 5 minutes, followed by incubation on ice for at least 5 minutes. For random hexamer containing reaction, the combined reaction mixture is further incubated at 23° C. for 10 minutes while for oligodT containing reaction this step is not included. Subsequently 1 μL of dithiothreitol (100 mM), RNaseOUT (40 units/μl), and Superscript IV (200 units/μl) are added to the reaction in total volume of 20 μl and continued at 50-55° C. for 10 minutes. The reaction is inactivated by incubating it at 80° C. for 10 minutes. The generated cDNA integrity is validated through GAPDH amplification. Reaction conditions are as described in the tables below (Table 2 and Table 3). Total isolated RNA from each region is used separately to generate cDNA for further PCR amplification. At least ~$10^{12}$ molecules of RNA (0.6 to 1 μg of RNA) are used from each region to cover the theoretical diversity. In order to prevent any storage related issues which might interfere with the RNA yield or quality, the total RNA isolation is completed on the same day of sample isolation with utmost care. The generated cDNA integrity is validated through GAPDH amplification. Post cDNA integrity validation of total cDNA generated is used for primary PCR amplification. No bands are obtained in the absence of a primer in the first strand cDNA reaction, indicating that the products resulted from the amplification of RNA and not DNA.

TABLE 2

| RT PCR reaction | | | | |
|---|---|---|---|---|
| | 1X | | 5X | |
| with superscript IV | Oligo dT (μL) | Random hexamer (μL) | Oligo dT (μL) | Random hexamer (μL) |
| RNA | 9 | 9 | 45 | 45 |
| OligodT/Random Hexamer | 2.5 | 2.5 | 12.5 | 12.5 |
| dNTPs | 1 | 1 | 5 | 5 |
| RT buffer 5X | 5 | 5 | 25 | 25 |
| DTT | 1 | 1 | 5 | 5 |
| RNase OUT | 1 | 1 | 5 | 5 |
| Superscript IV | 1 | 1 | 5 | 5 |

TABLE 3

| GAPDH PCR | |
|---|---|
| cDNA | 5 |
| dNTPs | 1 |
| 5X GC buffer | 10 |
| dH2O | 29 |
| GAPDH Reverse primer | 2 |
| GAPDH Forward primer | 2 |
| Phusion enzyme (2U/ul) | 1 |

Designing of Degenerate Primers:

The optimized design of the PCR primers for rearranged V-genes, are done to maximize the diversity of the PCR products. The primers are located at the 5' and 3' ends (Forward and Reverse primers respectively) of the mature V-regions, but do not incorporate internal restriction sites that mismatch the template and bias amplification. The primary Forward primers are designed to match for each of the families of human VH (9 primers) or Vk (6 primers) or Vl (11 primers) genes and reverse primers to match each of the human IgM or Ck or Cl segments. Further sets of secondary primers are designed to optimize the linking of VH and Vk, or Vl genes at random and append restriction sites to the linked genes. Reverse primers for secondary PCR are designed to tap the end of Jh or Jk or Jl segments. As heritable variation that exists in the composition of the antibody repertoire, four unique tri-nucleotide markers are incorporated into the designed secondary primers specifying the region based on language spoken and geographical location in India from where the donors are chosen and samples collected (FIG. 1). The tri-nucleotide markers listed as GCC, GCG, GCA and GCT triplets are specifically tagged in the heavy chain sub-families for regions 1, 2, 3 and 4 respectively. Heavy chain sub-families are chosen due to its highest theoretical diversity. All tri-nucleotide markers code for the identical amino acid i.e., alanine, and does not interfere with antibody conformation or antigen binding. The triplet, is strategically placed after the restriction site so that the marker can be retained even after transfer of phage clones to yeast. A set of reverse primers are designed containing fifth unique tri-nucleotide marker i.e., CAC, coding for valine. The amino acid valine is a conserved amino acid in framework 4 region of heavy chain. This is done specifically to track the source of molecules obtained against a specific antigen (Table 4 and Table 5).

TABLE 4

| Heavy Chains | Forward Primer | | Reverse Primer |
|---|---|---|---|
| Region 1 | | | |
| HuVH1B/7A-NcoI | 5'-GTC CTC GCA ACT CCA TGG ATG GCC CAG RTG CAG CTG GTG CAR TCT GG-3' | HuJH1/2-Rev | 5'-ACC GCC TCC ACC TCTAGA TGA GGA GAC GGT GAC CAG GGT GCC-3' |
| HuVH1C-NcoI | 5'-GTC CTC GCA ACT CCA TGG ATG GCCSAG GTC CAG CTG GTR CAG TCT GG-3' | HuJH3-Rev | 5'-ACC GCC TCC ACC TCTAGA TGA AGA GAC GGT GAC CAT TGT CCC-3' |
| HuVH2B-NcoI | 5'-GTC CTC GCA ACT CCA TGG ATG GCC CAG RTC ACC TTG AAG GAG TCT GG-3' | HuJH4/5-Rev | 5'-ACC GCC TCC ACC TCTAGA TGA GGA GAC GGT GAC CAG GGT TCC-3' |
| HuVH3B-NcoI | 5'-GTC CTC GCA ACT CCA TGG ATG GCC SAG GTG CAG CTG GTG GAG TCT GG-3' | HuJH6-Rev | 5'-ACC GCC TCC ACC TCTAGA TGA GGA GAC GGT GAC CGT GGT CCC-3' |
| HuVH3C-NcoI | 5'-GTC CTC GCA ACT CCA TGG ATG GCC GAG GTG CAG CTG GTG GAG WCY GG-3' | | |
| HuVH4B-NcoI | 5'-GTC CTC GCA ACT CCA TGG ATG GCC CAG GTG CAG CTA CAG CAG TGG GG-3' | | |
| HuVH4C-NcoI | GTC CTC GCA ACT CCA TGG ATG GCC CAG STG CAG CTG CAG GAG TCS GG-3' | | |
| HuVH5B-NcoI | 5'-GTC CTC GCA ACT CCA TGG ATG GCC GAR GTG CAG CTG GTG CAG TCT GG-3' | | |
| HuVH6A-NcoI | 5'-GTC CTC GCA ACT CCA TGG ATG GCC CAG GTA CAG CTG CAG CAG TCA GG-3' | | |
| Region2 | | | |
| HuVH1B/7A-NcoI | 5'-GTC CTC GCA ACT CCA TGG ATG GCG CAG RTG CAG CTG GTG CAR TCT GG-3' | HuJH1/2-Rev | 5'-ACC GCC TCC ACC TCTAGA TGA GGA GAC GGT GAC CAG GGT GCC-3' |
| HuVH1C-NcoI | 5'-TC CTC GCA ACT CCA TGG ATG GCG SAG GTC CAG CTG GTR CAG TCT GG-3' | HuJH3-Rev | 5'-ACC GCC TCC ACC TCTAGA TGA AGA GAC GGT GAC CAT TGT CCC-3' |
| HuVH2B-NcoI | 5'-GTC CTC GCA ACT CCA TGG ATG GCG CAG RTC ACC TTG AAG GAG TCT GG-3' | HuJH4/5-Rev | 5'-ACC GCC TCC ACC TCTAGA TGA GGA GAC GGT GAC CAG GGT TCC-3' |

TABLE 4-continued

| | Heavy Chains Forward Primer | | Reverse Primer |
|---|---|---|---|
| HuVH3B-NcoI | 5'-GTC CTC GCA ACT CCA TGG ATG GCG SAG GTG CAG CTG GTG GAG TCT GG-3' | HuJH6-Rev | 5'-ACC GCC TCC ACC TCTAGA TGA GGA GAC GGT GAC CGT GGT CCC-3' |
| HuVH3C-NcoI | 5'-GTC CTC GCA ACT CCA TGG ATG GCG GAG GTG CAG CTG GTG GAG WCY GG-3' | | |
| HuVH4B-NcoI | 5'-GTC CTC GCA ACT CCA TGG ATG GCG CAG GTG CAG CTA CAG CAG TGG GG-3' | | |
| HuVH4C-NcoI | 5'-GTC CTC GCA ACT CCA TGG ATG GCG CAG STG CAG CTG CAG GAG TCS GG-3' | | |
| HuVH5B-NcoI | 5'-GTC CTC GCA ACT CCA TGG ATG GCG GAR GTG CAG CTG GTG CAG TCT GG-3' | | |
| HuVH6A-NcoI | 5'-GTC CTC GCA ACT CCA TGG ATG GCG CAG GTA CAG CTG CAG CAG TCA GG-3' | | |
| Region 3 | | | |
| HuVH1B/7A-NcoI | 5'-GTC CTC GCA ACT CCA TGG ATG GCA CAG RTG CAG CTG GTG CAR TCT GG-3' | HuJH1/2-Rev | 5'-ACC GCC TCC ACC TCTAGA TGA GGA GAC GGT GAC CAG GGT GCC-3' |
| HuVH1C-NcoI | 5'-GTC CTC GCA ACT CCA TGG ATG GCA SAG GTC CAG CTG GTR CAG TCT GG-3' | HuJH3-Rev | 5'-ACC GCC TCC ACC TCTAGA TGA AGA GAC GGT GAC CAT TGT CCC-3' |
| HuVH2B-NcoI | 5'-GTC CTC GCA ACT CCA TGG ATG GCA CAG RTC ACC TTG AAG GAG TCT GG-3' | HuJH4/5-Rev | 5'-ACC GCC TCC ACC TCTAGA TGA GGA GAC GGT GAC CAG GGT TCC-3' |
| HuVH3B-NcoI | 5'-GTC CTC GCA ACT CCA TGG ATG GCA SAG GTG CAG CTG GTG GAG TCT GG-3' | HuJH6-Rev | 5'-ACC GCC TCC ACC TCTAGA TGA GGA GAC GGT GAC CGT GGT CCC-3' |
| HuVH3C-NcoI | 5'-GTC CTC GCA ACT CCA TGG ATG GCA GAG GTG CAG CTG GTG GAG WCY GG-3' | | |
| HuVH4B-NcoI | 5'-GTC CTC GCA ACT CCA TGG ATG GCA CAG GTG CAG CTA CAG CAG TGG GG-3' | | |
| HuVH4C-NcoI | 5'-GTC CTC GCA ACT CCA TGG ATG GCA CAG STG CAG CTG CAG GAG TCS GG-3' | | |
| HuVH5B-NcoI | 5'-GTC CTC GCA ACT CCA TGG ATG GCA GAR GTG CAG CTG GTG CAG TCT GG-3' | | |
| HuVH6A-NcoI | 5'-GTC CTC GCA ACT CCA TGG ATG GCA CAG GTA CAG CTG CAG CAG TCA GG-3' | | |
| Region 4 | | | |
| HuVH1B/7A-NcoI | 5'-GTC CTC GCA ACT CCA TGG ATG GCT CAG RTG CAG CTG GTG CAR TCT GG-3' | HuJH1/2-Rev | 5'-ACC GCC TCC ACC TCTAGA TGA GGA GAC GGT GAC CAG GGT GCC-3' |
| HuVH1C-NcoI | 5'-GTC CTC GCA ACT CCA TGG ATG GCT SAG GTC CAG CTG GTR CAG TCT GG-3' | HuJH3-Rev | 5'-ACC GCC TCC ACC TCTAGA TGA AGA GAC GGT GAC CAT TGT CCC-3' |
| HuVH2B-NcoI | 5'-GTC CTC GCA ACT CCA TGG ATG GCT CAG RTC ACC TTG AAG GAG TCT GG-3' | HuJH4/5-Rev | 5'-ACC GCC TCC ACC TCTAGA TGA GGA GAC GGT GAC CAG GGT TCC-3' |

TABLE 4-continued

| | Heavy Chains Forward Primer | | Reverse Primer |
|---|---|---|---|
| HuVH3B-NcoI | 5'-GTC CTC GCA ACT CCA TGG ATG CT SAG GTG CAG CTG GTG GAG TCT GG-3' | HuJH6-Rev | 5'-ACC GCC TCC ACC TCTAGA TGA GGA GAC GGT GAC CGT GGT CCC-3' |
| HuVH3C-NcoI | 5'-GTC CTC GCA ACT CCA TGG ATG GCT GAG GTG CAG CTG GTG GAG WCY GG-3 | | |
| HuVH4B-NcoI | 5'-GTC CTC GCA ACT CCA TGG ATG GCT CAG GTG CAG CTA CAG CAG TGG GG-3' | | |
| HuVH4C-NcoI | 5'-GTC CTC GCA ACT CCA TGG ATG GCT CAG STG CAG CTG CAG GAG TCS GG-3' | | |
| HuVH5B-NcoI | 5'-GTC CTC GCA ACT CCA TGG ATG GCT GAR GTG CAG CTG GTG CAG TCT GG-3' | | |
| HuVH6A-NcoI | 5'-GTC CTC GCA ACT CCA TGG ATG GCT CAG GTA CAG CTG CAG CAG TCA GG-3' | | |

Region 5

| | | | |
|---|---|---|---|
| HuVH1B/7A-NcoI | 5'-GTC CTC GCA ACT CCA TGG ATG GCC CAG RTG CAG CTG GTG CAR TCT GG-3' | HuJH1/2-Rev | 5'-ACC GCC TCC ACC TCTAGA TGA GGA GAC GGT CAC CAG GGT GCC-3' |
| HuVH1C-NcoI | 5'-GTC CTC GCA ACT CCA TGG ATG GCCSAG GTC CAG CTG GTR CAG TCT GG-3' | HuJH3-Rev | 5'-ACC GCC TCC ACC TCTAGA TGA AGA GAC GGT CAC CAT TGT CCC-3' |
| HuVH2B-NcoI | 5'-GTC CTC GCA ACT CCA TGG ATG GCC CAG RTC ACC TTG AAG GAG TCT GG-3' | HuJH4/5-Rev | 5'-ACC GCC TCC ACC TCTAGA TGA GGA GAC GGT CAC CAG GGT TCC-3' |
| HuVH3B-NcoI | 5'-GTC CTC GCA ACT CCA TGG ATG GCC SAG GTG CAG CTG GTG GAG TCT GG-3' | HuJH6-Rev | 5'-ACC GCC TCC ACC TCTAGA TGA GGA GAC GGT CAC CGT GGT CCC-3' |
| HuVH3C-NcoI | 5'-GTC CTC GCA ACT CCA TGG ATG GCC GAG GTG CAG CTG GTG GAG WCY GG-3' | | |
| HuVH4B-NcoI | 5'-GTC CTC GCA ACT CCA TGG ATG GCC CAG GTG CAG CTA CAG CAG TGG GG-3' | | |
| HuVH4C-NcoI | GTC CTC GCA ACT CCA TGG ATG GCC CAG STG CAG CTG CAG GAG TCS GG-3' | | |
| HuVH5B-NcoI | 5'-GTC CTC GCA ACT CCA TGG ATG GCC GAR GTG CAG CTG GTG CAG TCT GG-3' | | |
| HuVH6A-NcoI | 5'-GTC CTC GCA ACT CCA TGG ATG GCC CAG GTA CAG CTG CAG CAG TCA GG-3' | | |

TABLE 5

| | Light Chains Forward Primer | | Reverse Primer |
|---|---|---|---|
| | Kappa | | |
| HuVk1B-For-HindIII | 5'-ACC GCC TCC ACC AAG CTT GAC ATC CAG WTG ACC CAG TCT CC-3' | HuJk1Rev: | 5'ACC GCC TCC ACC GGCGCGCC ACG TTT GAT TTC CAC CTT GGT CCC |

TABLE 5-continued

| | Light Chains Forward Primer | | Reverse Primer |
|---|---|---|---|
| HuVk2-For-HindIII | 5'-ACC GCC TCC ACC AAG CTT GAT GTT GTG ATG ACT CAG TCT CC-3' | HuJk2Rev: | 5' ACC GCC TCC ACC GGCGCGCC ACG TTT GAT CTC CAG CTT GGT CCC |
| HuVk3B-FOR-HindIII | 5'-ACC GCC TCC ACC AAG CTT GAA ATT GTG WTG ACR CAG TCT CC-3' | HuJk3Rev: | 5' ACC GCC TCC ACC GGCGCGCC ACG TTT GAT ATC CAC TTT GGT CCC |
| HuVk4B-FOR-HindIII | 5'-ACC GCC TCC ACC AAG CTT GAT ATT GTG ATG ACC CAC ACT CC-3' | HuJk4Rev: | 5' ACC GCC TCC ACC GGCGCGCC ACG TTT GAT CTC CAC CTT GGT CCC |
| HuVk5-FOR-HindIII | 5'-ACC GCC TCC ACC AAG CTT GAA ACG ACA CTC ACG CAG TCT CC-3' | | |
| HuVk6-FOR-HindIII | 5'-ACC GCC TCC ACC AAG CTT GAA ATT GTG CTG ACT CAG TCT CC-3' | | |
| | Lambda | | |
| HuVl1A-FOR-HindIII | 5'-ACC GCC TCC ACC AAGCTT CAG TCT GTG CTG ACT CAG CCA CC-3' | HuJl1-1_Rev: | 5'ACC GCC TCC ACC GGCGCGCC ACC TAG GAC GGT GAC CTT GGT CCC-3' |
| HuVl1B-FOR-HindIII | 5'-ACC GCC TCC ACC AAG CTT CAG TCT GTG YTG ACG CAG CCG CC-3' | HuJl_2-3_Rev: | 5'ACC GCC TCC ACC GGCGCGCC ACC TAG GAC GGT CAG CTT GGT CCC-3' |
| HuVl1C-FOR-HindIII | 5'-ACC GCC TCC ACC AAG CTT CAG TCT GTC GTG ACG CAG CCG CC-3' | HuJl_4-5_Rev: | 5'ACC GCC TCC ACC GGCGCGCC ACC TAA AAC GGT GAG CTG GGT CCC-3' |
| HuVl2-FOR-HindIII | 5'-ACC GCC TCC ACC AAG CTT CAR TCT GCC CTG ACT CAG CCT-3' | | |
| HuVl3A-FOR-HindIII | 5'-ACC GCC TCC ACC AAG CTT TCC TAT GWG CTG ACT CAG CCA CC-3' | | |
| HuVl3B-FOR-HindIII | 5'-ACC GCC TCC ACC AAG CTT TCT TCT GAG CTG ACT CAG GAC CC-3' | | |
| HuVl4-FOR-HindIII | 5'-ACC GCC TCC ACC AAG CTT CAC GTT ATA CTG ACT CAA CCG CC-3' | | |
| HuVl5-FOR-HindIII | 5'-ACC GCC TCC ACC AAG CTT CAG GCT GTG CTG ACT CAG CCG TC-3' | | |
| HuVl6-FOR-HindIII | 5'-ACC GCC TCC ACC AAG CTT AAT TTT ATG CTG ACT CAG CCC CA-3' | | |
| HuVl7/8-FOR-HindIII | 5'-ACC GCC TCC ACC AAG CTT CAG RCT GTG GTG ACY CAG GAG CC-3' | | |
| HuVl9-FOR-HindIII | 5'-ACC GCC TCC ACC AAG CTT CWG CCT GTG CTG ACT CAG CCM CC-3' | | |

Primary PCR for Amplifying IgM Pool

Figure 3:
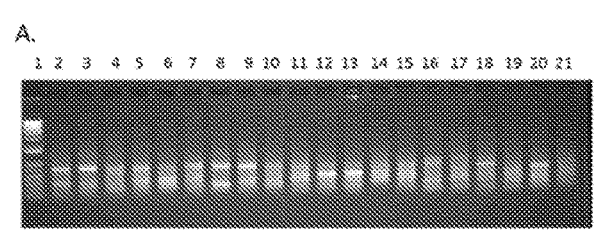
FIG. 3 illustrates Primary PCR amplification of antibody gene families from PBMC cDNA.
Figure 3:
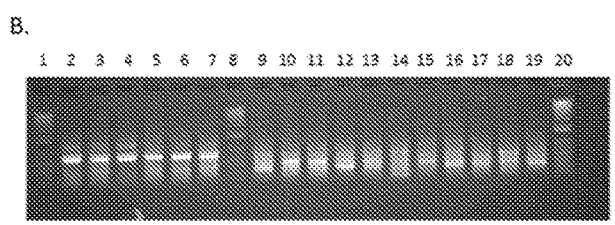

Primary PCR set up is done for each subfamily to tap the IgM pool which represents the naïve repertoire. For heavy chain, PCR set up is done in 50 µL volume as described in the table (Table 4) below in triplicates with a total volume of 150 µL. This set up is done for all the primer combinations. For light chain kappa and lambda families, the PCR reactions are carried out with various forward degenerate primers with constant Ck or Cλ reverse primers. There are mild sequence differences in Cλ reverse primers designing therefore both the primers are included individually in the PCR reactions set up. PCR reactions are performed for amplification with 18-25 cycles for 1-2 min at 94° C., 1-2 min at 50° C., and 50 s-90 s at 72° C. Low number of PCR amplification cycle is fixed with a notion to reduce the probability of PCR introduced mutation. Primary PCR amplicon for individual subfamilies of Vh, Vk and Vl are found to be of ~680 bp size. All the subfamilies of heavy chain and Light chain show expected amplification (FIG. 3).

TABLE 6

Primary PCR setup

| | 1X (μL) |
|---|---|
| cDNA | 5 |
| dNTPs | 1 |
| 5X GC buffer | 10 |
| dH$_2$O | 29 |
| Reverse primer | 2 |
| Forward primer | 2 |
| Phusion enzyme (2U/μl) | 1 |

Primers detail for 1° PCR

| | Heavy chain | Kappa Chain | Lambda Chain |
|---|---|---|---|
| Forward Primers | Hu VH1B/7A-H1 | HuVK1B-K1 | Hu VL1A-L1 |
| | Hu VH1C-H2 | HuVK2-K2 | Hu VL1B-L2 |
| | Hu VH2B-H3 | HuVK3B-K3 | Hu VL1C-L3 |
| | Hu VH3B-H4 | HuVK4B-K4 | Hu VL2-L4 |
| | Hu VH3C-H5 | HuVK5B-K5 | Hu VL3A-L5 |
| | Hu VH4B-H6 | HuVK6-K6 | Hu VL3B-L6 |
| | Hu VH4C-H7 | | Hu VL4-L7 |
| | Hu VH5B-H8 | | Hu VL5-L8 |
| | Hu VH6A-H9 | | Hu VL6-L9 |
| | | | Hu VL7/8-L10 |
| | | | Hu VL9-L11 |
| Reverse Primers | IgM_Rev | HuCK_Rev | HuCL2_Rev |
| | | | HuCL7_Rev |
| Forward and Reverse Primers for PCR control | | | |
| GAPDH | GAPDH | | |
| No template control | | | |

Purification of Primary PCR:

Primary amplicon from individual families are pooled and cleaned up using PCR-clean up kit. 5 volumes of Buffer PB i.e., 750 μl of Buffer PB is added to 1 volume of the PCR sample which is 150 μl of pooled PCR product. AQIAquick spin column in a provided 2 ml collection tube is placed followed by binding of DNA by centrifugation method. 750 μL of buffer PE is passed through followed by an empty spin to remove remaining of PE buffer. The cleaned DNA is eluted in 40 μL of nuclease free water. Concentration estimation for each subfamily is measured as 2-4 μg.

Figure 4:
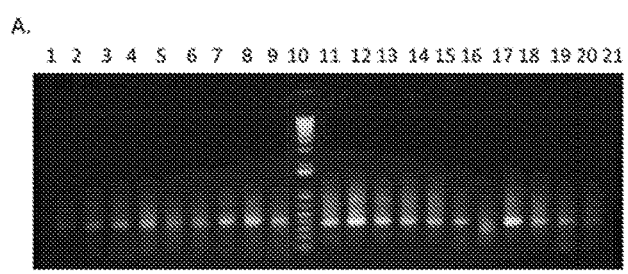
FIG. 4 illustrates Secondary PCR amplification of antibody gene families.
Figure 4:
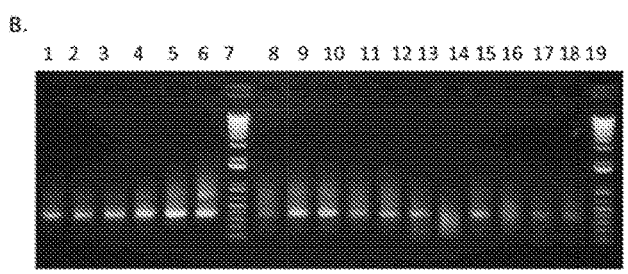

Secondary PCR to Enrich Naïve Population and Make it Compatible with In-House Vector:

Secondary PCR set up is done with 50-100 ng of primary amplicon as template. PCR conditions are kept similar to primary one. However, the primers are tagged with restriction sites for cloning into phagemid later on. For heavy chain families, the PCR reactions are carried out with various forward degenerate primers with restriction site i.e., NcoI. The reverse primers for heavy chain are to amplify region spanning from variable part to beginning of Jh segment, while restriction site is XbaI. For heavy chain, PCR set up is done in 50 μL volume as described in the tables below (tables 7 & 8) in triplicates with a total volume of 150 uL. This set up is done for all the primer combinations. For light chain kappa and lambda families, the PCR reactions are carried out with various forward degenerate primers with restriction site i.e., HindIII while AscI being the restriction site for reverse primer. PCR reactions are performed for amplification with 18 cycles for 1 min at 94° C., 1 min at 50° C., and 50 s at 72° C. Expected amplicon size of ~350-400 bp is seen indicating that only variable region is amplified (FIG. 4).

TABLE 7

Primers detail for secondary PCR

| Heavy chain Forward Primers | Reverse Primers | Kappa chain Forward Primers | Reverse Primers | Lambda chain Forward Primers | Reverse Primers |
|---|---|---|---|---|---|
| Hu VH1B/7A-H1 | JH1-2 | HuVK1B-K1 | JK1 | Hu VL1A-L1 | JL1 |
| Hu VH1C-H2 | | HuVK2-K2 | JK2 | Hu VL1B-L2 | |
| Hu VH2B-H3 | | HuVK3B-K3 | JK3 | Hu VL1C-L3 | |
| Hu VH3B-H4 | JH3 | HuVK4B-K4 | JK4 | Hu VL2-L4 | JL2-3 |
| Hu VH3C-H5 | | HuVK5B-K5 | JK5 | Hu VL3A-L5 | |
| Hu VH4B-H6 | JH4-5 | HuVK6-K6 | Mixture of all | Hu VL3B-L6 | |
| Hu VH4C-H7 | | | | Hu VL4-L7 | JL4-5 |
| Hu VH5B-H8 | | | | Hu VL5-L8 | |
| Hu VH6A-H9 | JH6 | | | Hu VL6-L9 | Mixture of all |
| | | | | Hu VL7/8-L10 | |
| | | | | Hu VL9-L11 | |

TABLE 8

| Secondary PCR set up | 1X |
|---|---|
| Primary PCR amplicon | 1 |
| dNTPs | 1 |
| 5X GC buffer | 10 |
| dH$_2$O | 33 |
| Reverse Primer | 2 |
| Forward Primer | 2 |
| Phusion Enzyme (2U/μL) | 1 |

Estimation of Secondary PCR Product:

All respective subfamilies are column cleaned followed by concentration estimation through bio-photometer. This is essential to have an estimate of amount of DNA in each pool which in turn will reflect the number of molecules going forward for library generation. Overall yield of Vh, Vk and Vl is ~30 μg and they are pooled in equimolar ratio.

Diversity Estimation of PCR Product:

Secondary PCR products are pooled according to the respective subfamilies (Vh, Vk and Vl). 1 ug of each subfamily is mixed separately with the mixture of 2 unit Taq DNA polymerase and 0.2 mM dATP. PCR extension reaction is performed for 20 min at 72° C. Extended products are purified by using PCR purification kit. 750 μL of Buffer PB is added to 1 volume of the PCR sample which is 150 μL of pooled PCR product. A QIAquick spin column in a provided 2 ml collection tube is placed followed by binding of DNA by centrifugation method. 750 μL of buffer PE is passed through followed by an empty spin to remove remaining of PE buffer. The cleaned DNA is eluted in 40 μL of nuclease free water. The DNA amount estimation is done using bio-spectrophotometer. Each subfamily is ligated into cloning vector individually by incubating with ligase enzyme at 4° C. overnight.

Figure 5:
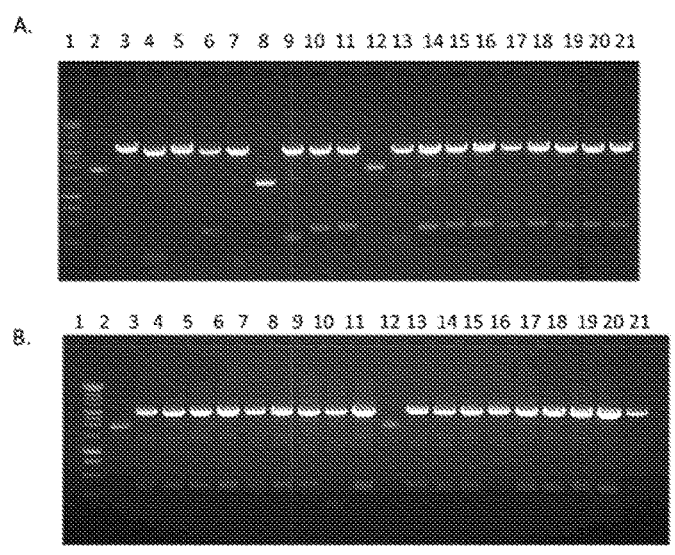
FIG. 5 illustrates Analysis of PCR pool from Antibody genes. (A) Heavy chain and Kappa Light chain genes, (B) Lambda light chain genes.

Before generating the actual library, it is essential to have an understanding/estimation of the functional diversity of the nucleotide pool. In order to do so, a fraction of amplicon from each V-family is cloned into cloning vector. Selected clones that are confirmed by restriction digestion (FIG. 5) are sent for peer-group sequencing. The sequencing result indicated that all the cloned molecules have different CDR sequences, length and are productive. There are few non-productive sequences also seen, however that is not significant enough. Sequences are categorized in to different families via in-silico approach using consensus sequences of heavy and light chains. The representative family members are seen in sequenced pool. Moreover, samples are PCR amplified and sent for deep sequencing to understand the complete depth of functional diversity.

Light Chain Cloning

5 μg of the kappa and lambda light chain from secondary PCR pool along with an in-house phagemid are digested with HindIII and AscI at 37° C. for overnight in a total volume of 100 μL. The digested samples are gel eluted followed by ligation set up at 4° C. for overnight (FIG. 6). The 25-50 ng of ligation mixture is transformed into 25 μL of TG1 cells through electroporation wherein 1.0 mm cuvette is used with an optimal setting of 1800 volts, 600 ohm and 10 pF. Post recovery in recovery media, 200 μL of transformed cells are spread on 144 mm plates and incubated overnight at 37° C. In total there are 6-8 plates from which colonies are scraped on following day and stocks are made with 20% glycerol. Transformation efficiency is calculated by dilution plating and found to be in the range of $10^8$ to about $10^{10}$, preferably at ~$10^8$.

The total numbers of cells are determined per vial of glycerol stocks through dilution plating and found to be $10^{12}$. Colonies are inoculated in 5 mL LB-Amp and plasmid is isolated. The isolated plasmids are checked for restriction digestion analysis. The insert release of ~300 bp confirmed the presence of light chain, both kappa and lambda in the pool.

One vial of light chain pool (both kappa and lambda) are inoculated in 100 mL of LB-Amp and grown for 2-3 hrs at 37° C. shaker-incubator followed by plasmid isolation by qiagen midi prep kit as per manufacturer's protocol. The midi prepped DNA for both the light chains are confirmed with restriction digestion analysis before proceeding with incorporation of heavy chain into it. The kappa and lambda light chain from secondary PCR pool along with an in-house phagemid are digested with HindIII and AscI followed by ligation and transformation individually into TG1, highly competent cells. As choice of antibody format, the Fab is preferred as this would prompt in developing rapid high through-put affinity-screening assays for crude antibody preparations.

Transformation efficiency of ~$10^8$ indicates a high number of independent clones present in the pool taping the diversity. Colonies are scraped and stored as glycerol stocks for future use. The estimated number of cells per vial is $10^{10}$, representing the complete diversity in excess. Few of the representative clones are used for plasmid isolation and confirmed by restriction digestion (FIG. 7) which indicated the ~100% presence of light chain insert. Separate Midi prep is done to isolate light chain library DNA, both kappa and lambda from the pool. Midi prep DNA is again confirmed through restriction digestion before used for further insertion of heavy chain pool. Tables 9 & 10 provide for components applicable for light chain cloning.

TABLE 9

| DNA | 5 μg |
|---|---|
| AscI-HF | 5 μL |
| HindIII-HF | 5 μL |
| Cut smart buffer(10X) | 10 μL |
| Milli-Q water | respectively volume of milli-Q water |
| Total volume | 100 μL |

TABLE 10

| DNA (vector) | 250 ng |
|---|---|
| DNA (insert) | 125 ng |
| T4 DNA ligase | 1 μL |
| T4 DNA ligase buffer(10X) | 5 μL |
| Milli-Q water | respectively |
| Total volume | 50 μL |

Heavy Chain Cloning:

5 μg of the kappa and lambda light chain library DNA along with secondary PCR pool of heavy chain are digested with NcoI and XbaI at 37° C. for overnight in a total volume of 100 μL. The digested samples are gel eluted followed by ligation set up at 4° C. for overnight (FIG. 8). The 25-50 ng of ligation mixture is transformed into 25 μL of TG1 cells through electroporation wherein 1.0 mm cuvette is used with an optimal setting of 1800 volts, 600 ohm and 10 pF. Post recovery in recovery media, 200 μL of transformed cells are spread on 144 mm plates and incubated overnight at 37° C. In total there are 6-8 plates from which colonies are scraped on following day and stocks are made with 20% glycerol and stored in −80° C. freezer. Transformation efficiency is calculated by dilution plating and found to be in the range of $10^8$ to about $10^{10}$, preferably at ~$10^8$.

The total numbers of cells are determined per vial of glycerol stocks through dilution plating and found to be $10^{12}$. Colonies are inoculated in 5 mL LB-Amp and plasmid is isolated. The isolated plasmids are checked for restriction digestion analysis with NcoI and XbaI for heavy chain and HindIII and AscI for Kappa & Lambda light chains. The insert release of ~400 bp confirmed the presence of heavy chain, in kappa (FIG. 9) and lambda pool (FIG. 10).

The heavy chain along with kappa and lambda light chain secondary PCR pool containing DNA library are digested individually with NcoI and XbaI followed by ligation and transformation individually into TG1, highly competent E. coli cells. Tables 11 & 12 provide for components applicable for heavy chain cloning.

TABLE 11

| DNA | 5 µg |
|---|---|
| Nco I-HF | 5 µL |
| Xba I-HF | 5 µL |
| Cut smart buffer(10X) | 10 µL |
| Milli-Q water | respectively volume of milli-Q water |
| Total volume | 100 µL |

TABLE 12

| DNA (vector) | 250 ng |
|---|---|
| DNA (insert) | 125 ng |
| T4 DNA ligase | 1 µL |
| T4 DNA ligase buffer(10X) | 5 µL |
| Milli-Q water | respectively |
| Total volume | 50 µL |

Cloning of Heavy Chain into Light Chain Library, Screening of Clones, Efficiency Estimation, Scraping of Cells, Glycerol Stock Preparation, Estimation of Cells/Vial:

Transformation efficiency of about $10^8$ to about $10^{10}$, preferably ~$10^9$ indicates a high number of independent clones present in the pool taping the diversity. Colonies are scraped and stored as glycerol stocks for future use. The estimated number of cells per vial is $10^{12}$ representing the complete diversity. Few of the representative clones are used for plasmid isolation and confirmed by restriction digestion which indicated the ~90% presence of both heavy chain and light chain insert confirm the presence of Fab format. Selected clones are optionally sent for peer group sequencing. The sequencing result indicates that >80% of the cloned molecules are functional (FIG. 11) and are having different CDR sequences and lengths ranging from 4 to 22 amino acids. Few non-productive sequences also seen, however that is not significant enough. This indicates a complete transfer of diversity from naïve B-cell repertoire in to bacterial library through PCR pool.

Phage Library Generation:

1 ml of kappa and lambda bacterial glycerol stock are grown into 200 ml LB-AMP medium at 37° C. until OD at 600 nm reaches 0.8. Further, M13KO7 helper phage at multiplicity of infection (MOI) of 10 to the bacteria is added and incubated at 37° C. for another 30 minutes. Post infection, infected bacteria is centrifuged and the pellet is re-suspended into 200 ml of LB with 100 µg/ml ampicillin and 25 µg/ml kanamycin followed by growth at 30° C. for overnight at 250 rpm. Suspension is spun down at 8000 rpm for 15 min at 4° C. followed by discarding the pellet. Separated supernatant is mixed with PEG/NaCl solution in ¼ volume of supernatant and the mixture is incubated on ice for 1 h. The mixture is centrifuged at 10000 g for 15 min and the phage pellet is re-suspended into 20 ml of PBS. Glycerol is added to a final concentration of 50% to the entire phage suspension and frozen in aliquots of 1 ml at −80° C. as phage library stock.

Glycerol stocks of both kappa and lambda bacterial library are mixed and inoculated and used for phage library generation. With addition of helper phage, the phage particles displaying the diversity are precipitated and purified, and stored as glycerol stocks for future use. The estimated number of phage library that is derived from plaque forming assay, is found to be about $10^{10}$ to about $10^{11}$, preferably ~$10^{11}$ pfu/mL (FIG. 12).

Screening of Library/Strategy for Panning:

Screening of naïve library is the most important step as this will produce the stream of potential binders against specific target antigen. Taking the whole process of generation and developing the binders into mind, the aim of panning is to remove the non-specific binders from the pool of naïve repertoire. Therefore, the phage screening strategy consisting of binding, amplification and restriction digestion and sequence confirmation steps needs to be carefully decided. In addition to having an efficient binding, the ratio of antigen and phage molecules is also to be decided accordingly to avoid any kind of biasness during binding.

A library of phage-displayed antibodies contains clones that bind to a target better than other clones and clones that amplify faster than other clones. These characteristics are mostly independent. This also indicates that a longer period of amplification might drive towards loss of diversity of binders. Moreover, there might be an enrichment of target unrelated antibodies.

Keeping the above mentioned criteria in practice, the ratio of antigen molecules to phage particles is kept at least 10-100 times higher. To avoid any sort of non-specific binder's enrichment, the amplification is kept for not more than 90 minutes.

Estimation of Phage Number:

A single colony from the TG1 bacterial plate is inoculated in bacteria in 3 ml LB medium and grown at 37° C. until OD600≈0.9. 0.7% of agarose is prepared in MQ water and stored at 50° C. in aliquots of 3 ml each in a 15 ml of falcon tubes. The phage supernatant and pellet are diluted at respective steps from $10^{-1}$ to $10^{-4}$. 100 ul of diluted phage and 100 µl TG1 cells are added in to each of agarose aliquots and mixed followed by immediately spreading on LB Agar plate. The plates are incubated in 37° C. incubator for overnight. The plaque formation is observed and counted on next day. The number of panned molecules is calculated based on number of plaques observed.

Bead Conjugation:

Dyna beads are weighed at a quantity of 0.5 mg corresponding to ~$10^8$ beads and dissolved into 0.1 M sodium phosphate buffer, pH 7.4. This suspension is vortexed for 30 sec followed by incubation at room temperature for 10 min with continuous rotation. The suspension is washed twice with 0.1 M sodium phosphate buffer and resuspended again into 100 µL of 0.1 M sodium phosphate buffer. Her2, ligand solution, (100 µL) is added the 10 µg of to the bead suspension. Further, the suspension is mixed well before adding the 100 µL of ammonium sulfate solution (3 M ammonium sulfate). The mixture is incubated for 20 h at 37° C. with slow tilt but continuous rotation. Post incubation the tube is placed on the magnet holder for 1 min for magnetic separation. The magnet holder (with the tube in place) is carefully turned upside-down twice to ensure no beads remain in the cap. The supernatant is removed and beads are washed four times with 1 mL 1×PBS containing BSA (0.05%). Finally, the beads are re-suspended in 100 μL of 1×PBS with BSA (0.05%) and are used in panning.

Bead Conjugation Efficiency by FACS:

In order to perform magnetic separation based approach for panning, generation of antigen coated magnetic beads is done. The conjugation efficiency is determined using Flow cytometer (FIG. 13). Purified Her2 is used as the antigen. The experiments start with an incubation of ~$10^5$ beads with various combinations of antibody. Herein the antibody which binds with the ligand is labeled with biotin. N-Hydroxysuccinimide (NHS) ester-activated biotins are the most popular type of biotinylation reagent. NHS esters react efficiently with primary amino groups (—NH) in pH 7-9 buffers to form stable amide bonds. Because antibodies and other proteins generally contain multiple lysine (K) residues in addition to the N-terminus of each polypeptide, they have multiple primary amines available as targets for labeling with NHS-activated reagents. The extent of biotin labeling depends on the size and distribution of amino groups on the protein and the amount of reagent used. 10 mM Biotin solution is made by mixing 2.2 mg of Sulfo-NHS-Biotin with 500 μL of water. Trastuzumab, Anti-Her2 antibody, solution in 1×PBS is made at a concentration 2 mg/mL. 27 μL of biotin solution is added to 1 mL of trastuzumab followed by incubation for 2 hr on ice. Thermo Scientific ZebaSpin Desalting Column is used to desalt the excess and unbound biotin molecules from the solution. The protein concentration is estimated using a spectrophotometer and the concentration is found to be with insignificant change. Rituximab, a non-specific antibody is also biotinylated and the concentration estimation to post biotinylation is 2 mg/mL. Streptavidin with Alexa 633 fluorophore is used as secondary antibody to tap the extent of biotinylation. 1 μL of bead alone and bead coated with Her2 ligand are mixed with no antibody, biotinylated trastuzumab, biotinylated rituximab at a concentration of 0.05 mg/mL followed by volume make up to 100 μL with 1×PBS containing 0.5% BSA. The mixture is incubated for 2 hrs on ice followed by a washing with 1×PBS containing 0.5% BSA. Finally the beads are re-suspended in 25 μL of streptavidin-alexa633 solution in 1×PBS containing 0.5% BSA and volume is increased to 500 uL before readings are taken. All the flow experiments are done by using Accuri C6 flow cytometer while the analysis is done by using BD Accuri C6 software. Firstly forward and side scatter data is seen to fix a gate followed by fluorescence reading through FLH4 filter. At least 10000 data points are collected for each sample.

Panning:

Single colony from the freshly streaked TG1 bacterial plate is inoculated into 3 ml LB medium followed by incubation at 37° C. until OD600≈0.9 and this is used for phage infection later. 100 μl 0.5% MPBS is added to the 100 μl suspension of antigen conjugated magnetic beads and incubated for 2 hr at room temperature. A phage library aliquot is thawed and the phage particles are precipitated with 250 μl (¼ of the phage suspension volume) PEG/NaCl solutions (20% PEG 8000 and 2.5 M NaCl) and incubated on ice for 30 min followed by centrifugation of the precipitated phage at 10,000×g for 10 minutes. The supernatant is discarded and the phage pellet is re-suspended in 200 Il PBS solution. Phage suspension (200 μl) is added to the conjugated bead with antigen and incubated on a rotator at room temperature for 2 h. The beads are washed at least two times with 1 ml 0.05% PBST (0.05% Tween-20 in PBS). Finally, magnetic beads bound with phage particle binders are re-suspended in 100 μl PBS. 10 μL of beads suspension is kept aside for plaques assay later on. The remaining 90 μl of the suspension is added to 2 ml of grown TG1 cells prepared earlier and the mixture is incubated at 37° C. for 1 h. Post incubation it is diluted into 10 ml LB medium containing ampicillin at a final concentration of 25 μg/ml. After two more hours of incubation at 37° C. with shaking at 250 rpm, concentration of ampicillin is increased to a final concentration of 100 μg/ml. M13KO7, helper phage, is mixed into the amplified TG1 cells with an MOI of 10 and incubated at 37° C. for another 30 minutes. Helper phage-infected bacteria is spun down and the pellet is re-suspended into 10 ml of LB medium supplemented with 100 μg/ml ampicillin and 25 μg/ml kanamycin followed by incubation at 30° C. for 90 minutes for phage amplification. The bacterial culture is pelleted down by centrifugation for 10 min at 10,000 g. The pellet is discarded and supernatant is used for precipitation of amplified phage molecules by adding PEG/NaCL solution to the supernatant (¼th volume of supernatant). The mixture is incubated for 30 min on ice, followed by spinning the precipitated phage at 10,000 g for 10 minutes. Supernatant is discarded and pellet is re-suspended in 1 ml of PBS. The Plaques assay is performed from the 10 μL of amplified phage suspension to estimate the amplified phage number while the remaining of the precipitated phage are stored with 50% glycerol at −80° C. freezer for long term storage.

Plaque assay is performed at every step to ensure the numbers of phage particles. A single colony from the TG1 bacterial plate is inoculated in bacteria in 3 ml LB medium and is grown at 37° C. until OD600~0.9. 0.7% of agarose is prepared in MQ water and stored at 50° C. in aliquots of 3 ml each in a 15 ml of falcon tubes. The phage supernatant and pellet are diluted at respective steps from $10^{-1}$ to $10^{-4}$. 100 μl of diluted phage and 100 μl TG1 cells are added in to each of agarose aliquots and mixed followed by immediately spreading on LB Agar plate. The plates are incubated in 37° C. in an incubator for overnight. The plaque formation is observed and counted on next day. The number of panned molecules is calculated based on number of plaques observed (FIG. 14).

Isolation of Phage ssDNA and Amplification of Heavy and Light Chain Diversity Through PCR:

One vial of amplified phage is thawed and 200 μl of 20% PEG/2.5 M NaCl along with 5 μg of salmon sperm DNA is added to it by inverting the mixture several times, followed by letting it stay at 4° C. for 2 hr. (In order to transfer the panned pool to yeast display system for further selection and sorting, the ssDNA of the binders have to be isolated in enough quantity so that it represents the panned diversity. The use of sheared and boiled salmon sperm DNA specifically improves the yield of panned ssDNA.) Salmon sperm DNA is sheared and boiled before use. Salmon DNA is weighed and mixed with nuclease free water to a concentration of 5 mg/mL. The DNA is sheared with gentle mixing for 3 times with a 22 gauge needle followed by boiling for 5 minutes. Further the fragmented DNA is stored in aliquots at −20° C. for future use. The mixture, containing phage, PEG/NaCl and salmon sperm DNA, is centrifuged at 14,000×rpm for 10 minutes at 4° C. and the supernatant is discarded. Point to be noted here is that in case of no phage pellet seen, mixture is re-spun briefly at same speed. The supernatant is carefully pipetted out leaving only pellet. The pellet is re-suspended thoroughly in 100 μl of Iodide Buffer (10 mM Tris-HCl (pH 8.0), 1 mM EDTA, 4 M sodium iodide (NaI) by vortexing the tube. 250 μl of 100% ethanol is added and incubated overnight at −80° C. The preparation is centrifuged at 14,000 rpm for 30 minutes at 4° C., and supernatant is discarded. The pellet is washed twice with 0.5 ml of 70% ethanol followed by air drying the pellet. The pellet containing SSDNA is re-suspended in 20 μL of nuclease free water.

PCR amplification is done with specific set of Vh, Vl and Vk primers and is amplified to correct size which is ~500 bp for Vh while 450 bp for Vk and Vl (FIG. 15). The use of PCR cycles is kept in limited number avoiding the chances of PCR mediated incorporation of mutations. The amplicons are gel eluted and digested with NcoI and NotI for Vh while for Vk or Vl, HindIII and AscI are used. The PCT set-up details are provided in Table 13.

TABLE 13

PCR setup

|  | 1X (μL) | 3X (μL) |
|---|---|---|
| SSDNA | 1 | 3 |
| dNTPs | 1 | 3 |
| 5X GC buffer | 10 | 30 |
| dH$_2$O | 23 | 69 |
| Reverse primer (H/K/L) | 2 | 6 |
| Forward primer (H/K/L) | 2 | 6 |
| Phusion enzyme (2U/μl) | 1 | 3 |

Construction of Heavy and Light Chain Libraries in to Yeast Shuttle Vectors:

The plan of the whole strategy is to transfer the specific binders from phage to yeast expression vectors in order to do the screening and sorting in yeast system. An affinity based method is employed using a compatible method i.e., FACS to further select and rank the best binders.

As choice of antibody format, the Fab is preferred as this would prompt to develop rapid high through-put affinity-screening assays for crude antibody preparations. The Fab library is developed by exploiting the mating system wherein light chain library and heavy chain library is cloned in different yeast expression vectors. However, the kappa and lambda light chain PCR pool of panned molecules along with the in-house yeast expression vector exclusively designed and generated for light chains are digested with HindIII and AscI followed by ligation and transformation individually into TG1, highly competent cells.

Likewise, HC chain pool and the respective vector are digested with NcoI and NotI followed by ligation and transformation into TG1, highly competent cells. Transformation efficiency obtained for both heavy and light chain panned library are >10$^7$ cfu. In addition to these vectors, there are several expression vectors that are generated with exclusive features that are common to all vectors; on the contrary, though formats of antibody fragments displayed on yeast surface might vary but the transferred variable pool remain constant throughout.

Obtained transformed colonies for both heavy and light chain libraries are checked for insert release using NcoI/NotI for heavy chain and HindIII/AscI for light chain before they are scraped for glycerol stock preparation. Insert release for both the chains confirmed the presence of panned molecules. Glycerol stocks are stored at −80° C. for future use. Tables 12, 13 and 14 provide for components applicable in constructing libraries in yeast vector.

TABLE 14

| DNA | 5 μg |
|---|---|
| Nco I-HF | 3 μL |

TABLE 14-continued

| Not I-HF | 3 μL |
|---|---|
| Cut smart buffer(10X) | 10 μL |
| Milli-Q water | respectively volume of milli-Q water |
| Total volume | 100 μL |

TABLE 15

| DNA | 5 μg |
|---|---|
| Asc I | 3 μL |
| Hind III-HF | 3 μL |
| Cut smart buffer(10X) | 10 μL |
| Milli-Q water | respectively volume of milli-Q water |
| Total volume | 100 μL |

TABLE 16

| DNA (vector) | 250 ng |
|---|---|
| DNA (insert) | 125 ng |
| T4 DNA ligase | 1 μL |
| T4 DNA ligase buffer(10X) | 5 μL |
| Milli-Q water | respectively |
| Total volume | 50 μL |

The above ligation mix was incubated at 4° C. overnight, cleanup with PCR purification kit and transformed into TG1 by electroporation method.

Transformation of Heavy Chain and Light Chain Library:

Large amount of plasmid DNA isolation is done for both the libraries followed by restriction digestion with respective enzymes for confirmation (FIGS. 16 and 17). Upon validation, the 1 μg of each DNA is taken and transformed into yeast cells at ~5×10$^6$-2×10$^7$ cells/ml by electroporation method. Regarding the strains for transformation, EBY100 is used as a host for the cell surface display of the heavy chain library while YVH10 is used to express light chain library.

More specifically, Yeast cells in 5 ml YPD broth are grown overnight at 30° C. with shaking. Overnight culture is diluted up to OD600~0.2-0.3 in to 10 ml and grown until mid-log phase (~5×10$^6$-2×10$^7$ cells/ml or OD600 of 0.8-1.0). The mid-log phase cells are pelleted at 500 g for 4 minutes and the supernatant is discarded. 1 ml of EZ 1 solution is added to wash the pellet. The cells are re-pelleted and the supernatant is discarded. 500 μl EZ 2 solution is added to re-suspend the pellet. 400 μl of competent cells is mixed with 1 μg DNA (in less than 5 μl volume); 500 μl EZ 3 solution is added and mixed thoroughly. Said is incubated at 30° C. for 1-1.30 hr. During this incubation, mixing vigorously by flicking with finger or vortexing every 15-20 mins is carried out. 100 μl of the above transformation mixture is plated on an appropriate drop out synthetic glucose plate. The plates are incubated at 30° C. for 2-4 days to allow for growth of transformants. Both heavy chain and light chain panned library are successfully transformed in to yeast strains (EBY100-ura3Δ and YVH10) with an efficiency of >10$^6$.

Construction of Yeast Diploid Library Through Yeast Mating:

In order to display Fab format of library on the surface, mating of the two grown haploid cells representing heavy chain and light chain libraries is performed by mixing equal numbers of haploid cells. The mating efficiency is calculated as the number of diploid colonies in the double-selective plates divided by the number of total colonies in the single selective plates wherein the calculated mating percentage is ~40%. Further the diploid cells are enriched in double drop out media (ura$^-$, Trp$^-$) prior to any growth and expression analysis.

More specifically, EBY100-ura3Δ (MATα) transformants containing HC panned library in to p414GAL1 and the YVH10 (MATα) transformants containing LC panned library in to p416GAL1 are grown overnight at 30° C. and 220 rpm in 5 ml of the Trp drop out glucose and Ura drop out glucose medium respectively. Then the haploid cells are re-inoculated at the initial cell OD600~0.3 to freshly prepared above selective medias and grown until they reach optical densities ~1.2-1.8. Mating of the two grown haploid cells is performed by mixing equal numbers of cells (1.0 OD) by vortexing, spreading them on YPD agar plate and incubating at 30° C. for overnight. Cells are collected by gentle scraping with 1 ml of the double-selective Ura Trp double drop out glucose medium and pelleted by centrifugation (2,500 g for 3 min). The cells are washed by resuspension with 1 ml of sterilized cold deionized water and centrifuged to remove remaining media components. To estimate the mating efficiency, the washed cells are resuspended in a total volume of 1 ml of Ura Trp double drop out glucose medium, serially diluted, and spread out onto double-selective Trp Ura double drop out glucose agar, Trp drop out glucose agar and Ura drop out glucose agar plates. Plates are incubated at 30° C. for 2-3 days and the number of colonies are counted. Percentage mating efficiency is calculated as the number of diploid colonies in the double-selective plates divided by the number of total colonies in the single selective plates. To enrich diploids, cells are then inoculated to Trp Ura double drop out glucose medium at the very low cell density of OD600=0.1 and grown at 30° C. for 24 h, whenever required.

Antibody Gene Expression and Flow Sorting Analysis of Yeast Cells:

*Saccharomyces cerevisiae* 2N library having plasmids expressing heavy chain pool and light Chain pool are inoculated into 10 ml of Ura TrpSDCAA double drop out media and grown overnight at 30° C. (16-20 hrs). The OD600 nm of the overnight grown culture is measured and inoculated accordingly in 10 ml SDCAAUra Trp double drop out glucose media (uninduced culture) and 10 ml 2×SGCAA media (induced culture) such that the final OD600 nm becomes 0.2 to 0.3. Uninduced and induced cells are grown for different time points ranging from 24 to ~48 hr at 20° C.

For sorting studies, Antigen binding is monitored using biotinylated antigen (Her2) and selected and sorted based on positive events for double staining that is heavy chain and biotinylated antigen. 10 mM Biotin solution is made by mixing 2.2 mg of Sulfo-NHS-Biotin with 500 μL of water. Antigen, Her2 solution in 1×PBS is made at a concentration 1 mg/mL. 20 fold molar excess measuring 0.28 mM biotin solution is added to 1 mL of Her2 solution to initiate the reaction followed by an incubation for 2 hr on ice. Thermo Scientific ZebaSpin Desalting Column is used to desalt the excess and unbound biotin molecules from the solution. The concentration of Biotinylated Her2 is found to be 0.56 mg/mL. A concentration of 500 nM of biotinylated antigen is used to perform the binding experiments. Yeast diploid library having plasmids expressing heavy chain pool and light chain pool are inoculated into 10 ml of Ura Trp double drop out glucose media and grown overnight at 30° C. (16-20 hrs). The OD600 nm of the overnight grown culture is measured and inoculated accordingly in 10 ml Ura Trp double drop out glucose media (uninduced culture) and 10 ml Ura Trp double drop out galactose media (induced culture) such that the final OD600 nm becomes 0.2 to 0.3. Uninduced and induced yeast cells are grown for different time points ranging from 24 to 48 hr at 20° C. For resorting, the Yeast cells are collected, grown in to YPD medium and further plated on Ura-Trp-double drop out glucose plate and incubated at 30° C. for 2-3 days. Diploids yeast cells grown on Ura-Trp-glucose plate, are resorted through Flow cytometry with similar procedure mentioned above and repeated after 24 hours of induction at 20° C.

For all flow analyses, labeling Buffer, 1×PBS containing 0.5% BSA, is prepared followed by transfer of 4×10$^5$ cells (induced/un-induced) into 100 μl LB. The cells are spun down at 10000 rpm for 2 min at 4° C. The supernatant is carefully removed without disturbing the cells. 25μl of primary antibodies (Anti-His for Light Chain, Anti-c-Myc antibody for heavy chain and STREP-Alexa 633 for biotinylated Her2) were added to the samples and incubated at 4° C. for 30 minutes (All preparations of antibody dilutions to be done in labelling buffer). Another 100 μl of labeling buffer is added to the sample tubes followed by washing the cells twice with labeling buffer. 25 μl of secondary antibody conjugated with fluorophore is mixed to the sample tubes. The samples are incubated at 4° C. for 20 minutes. The cells are washed twice as mentioned above with 100 μl labeling buffer and the cells are re-suspended in 350 μl of 1×PBS followed by analysis of the samples on a flow-cytometer (FIG. 18).

The expression of light chain and heavy chain are observed in significant percentages. The light chain expression are probed by anti-His antibody and found to be >7% (FIG. 18) while heavy chain which is probed with anti-c-Myc antibody are found to be appearing in double positive quadrant with biotinylated Her2 at a percentage of 7.2 (FIG. 18). This result indicates the Fab formation and successful binding of the same with target antigen. In addition, while sorting the light chain marker anti-His and V5 tag are also explored and found to be positive against Her2 antigen staining while the percentage is being ~4% (FIG. 19). This is in accordance with the results found and shared by other researchers. This result also indicates that the dual auxotrophic marker selected diploids express light chain associated with the heavy chain.

Amplification of Heavy Chain and Light Chain from Diploids:

Yeast diploid colonies grown on Ura-Trp-glucose plate are used to amplify heavy chain and light chain. For Colony PCR, the cells are treated with 0.1% SDS at 95° C. for 5 min. The cells are then spun down and the supernatant is used as the template. The PCR amplified samples are purified and then gel eluted and sent for sequencing. Appearance of amplicons with respective sizes indicated that the cells are truly diploid and contains both heavy chain and light chain (FIG. 20). As confirmatory test, a PCR based experiment is performed wherein the heavy chain and light chain are amplified with specific pair of primers. Two sets of primers for VH and VL are used (Table 17). The sequence results are analyzed and the results match that of the variable region of the heavy and light chain of antibodies.

TABLE 17

| | |
|---|---|
| LC amplification | 5' GCTTCAGTTTTAGCACCATGG 3' |
| | 5' GCTGTGCCCCCAGAGGTGCTC 3' |
| HC amplification | 5' GCTTCAGTTTTAGCACCATGG 3' |
| | 5' CGATGGGCCCTTGGTGGAGGC 3' |

In Vitro Binding Studies of Sorted Library Pool with Her2 Antigen:

Yeast combinatorial library is created by mating of haploid cells and used further for selection against Her2, target antigen. Double positive cells for Her2 binding and c-Myc are sorted in to YPD medium and further plated on Ura-Trp-double drop out glucose plate and incubated at 30° C. for 2-3 days. Further, the cells are inoculated in Trp-Glucose media (Uninduced) and Trp-Galactose media (Induced). After 48 hrs of induction, the OD of the cultures is measured. Different cell numbers ($1.2 \times 10^7$, $2.4 \times 10^7$, $4.8 \times 10^7$) are used for TEV protease cleavage and each is treated with 1 unit, 5 units and 10 units of the enzyme. The reaction mixes are prepared as follows.

TABLE 18

|  | 1 Unit Enzyme | 5 Units Enzyme | 10 Units Enzyme |
|---|---|---|---|
| Water | 93 μL | 89 μL | 84 μL |
| 20X Buffer | 5 μL | 5 μL | 5 μL |
| DTT | 1 μL | 1 μL | 1 μL |
| TEV Enzyme (1 unit/μL) | 1 μL | 5 μL | 10 μL |
| Reaction volume | 100 μL | 100 μL | 100 μL |

The reaction mixture is incubated at 30° C., 220 rpm for 4.5-5 hrs. Post incubation, the samples are centrifuged at 4000 rpm for 10 min and the supernatants are stored at 2-8° C.

For ELISA experiment, the plates are coated with 50 uL of 1 ug/mL Her2 for overnight at 2-8° C. The coated plates are washed twice with 200 μL of PBST, followed by 2 hour incubation with 300 μL of blocking buffer on a rocker. This is followed by 200 uL PBST washes for two times. The plates are dried and stored at 2-8° C.

The plates are again washed twice with 200 ul PBST. Different dilutions of the sample (supernatant collected after TEV cleavage) are added to the plate and incubated at room temperature in rocking for 1 hour followed by two times PBST washes of 200 μL. Samples are incubated with the primary antibody at room temperature for 1 hr in rocking condition followed by PBST washes. Further the samples are incubated with secondary Antibody at room temperature. The plates are then washed with 200 μL PBST and the reaction is developed using 100 μL of TMB substrate. Post development, the reaction is stopped with 50 μL of 1N $H_2SO_4$. Herclon® is used as the standard for ELISA and processed as mentioned above.

The yeast constructs are generated in such a way so that they can be released from the anchor protein i.e., Aga2p, by TEV protease cleavage. The released antibody fragment is used for binding studies in vitro. This feature is introduced in the strategy to aid the affinity based selection of clones.

To release the fragments of antibody, various numbers of yeast cells ranging from $1.2 \times 10^7$ to $4.8 \times 10^7$ are treated with 1 unit, 5 units and 10 units of the TEV protease enzyme and released antibody is further confirmed by ELISA and SPR experiments.

ELISA experiments are done against Her2 antigen coated plates wherein the anti-FLAG to probe heavy chain and Herclon® to probe Her2 antigen directly are used as secondary antibody. For binding reaction increasing volume of TEV protease treated supernatant is used.

Identical preparation is used for Her2 binding experiments using Biacore. Appropriate controls are also run to rule out any misleading response. Increasing binding response is observed for both ELISA and Biacore experimental results (FIGS. 21 and 22).

Advantages of the Approach Employed by the Instant Disclosure:

1. The naïve library obtained by the method of the instant disclosure will harbor higher antibody diversity considering that the samples are collected from genetically diverse populations, preferably Indian population. The diversity of samples in this study will allow searching for population specific antibody repertoire. This is currently an untapped resource in antibody library space.
2. The instant disclosure employs a unique combination of phage and yeast antibody surface display, which allows to screen large library size (more than $10^9$ clones) and facilitates better folding of antibody structure because of yeast post translational modifications.
3. The library will incorporate antibody rational designing for high antibody stability, lesser antibody aggregation, lesser immunogenicity, better solubility and other antibody characteristics for improved manufacturability of said antibody.
4. The instant disclosure adopts an exclusive screening methodology wherein phage display screening is employed to remove only non-binders while subsequent yeast screening is employed to execute affinity based selection of the binders.
5. The instant disclosure also incorporates specific trinucleotide marker indicative of specific source of population which enables to trace back the source population later on, if needed, to screen for more hits.
6. The vectors used for phage and yeast surface expression are unique.
7. The clones selected from phage library will be transferred to yeast library in different antibody formats including ScFv or Fab without any PCR amplification and thereby retaining the original diversity with improved screening process.
8. The instant disclosure also provides flexibility in accommodating multiple changes in Fab sequences at each display platforms and flexibility of transferring panned molecules in Fab format to yeast expression system via combinatorial and non-combinatorial approaches.

Although disclosure and exemplification has been provided by way of illustrations and examples for the purpose of clarity and understanding, it is apparent to a person skilled in the art that various changes and modifications can be practiced without departing from the spirit or scope of the disclosure. Accordingly, the foregoing descriptions and examples should not be construed as limiting the scope of the present disclosure.

The description of the embodiments of the present disclosure reveals the general nature of the embodiments that are readily suitable for modification and/or adaptation for various applications by applying the current knowledge. Such specific embodiments of the disclosure, without departing from the generic concept, and, therefore, such adaptations and modifications should and are intended to be comprehended and considered within the meaning and range of equivalents of the disclosed embodiments.

It is also to be understood that the phrases or terms employed herein are for the purpose of description and not intended to be of any limitation. Throughout the present disclosure, the word "comprise", or variations such as "comprises" or "comprising" wherever used, are to be understood to imply the inclusion of a stated element, integer or step, or group of elements, integers or steps, but not the exclusion of any other element, integer or step, or group of elements, integers or steps.

Where a numerical limit or range is stated herein, the endpoints are included. Also, values and sub-ranges within a numerical limit or range are specifically included as if explicitly written out.

With respect to the use of any plural and/or singular terms in the present disclosure, those of skill in the art can translate from the plural to the singular and/or from the singular to the plural as is considered appropriate to the context and/or application. The various singular/plural permutations may be expressly set forth herein for the sake of clarity.

Any discussion of documents, acts, materials, devices, articles and the like that has been included in this specification is solely for the purpose of providing a context for the present disclosure. It is not to be taken as an admission that any or all of these matters form a part of the prior art base or are common general knowledge in the field relevant to the present disclosure, as it existed anywhere before the priority date of this application.

The contents of all references, patents, and published patent applications cited throughout this application are incorporated herein by reference for all purposes.

We claim:

1. A method of generating a naïve monoclonal antibody gene expression library, or a screened naïve monoclonal antibody gene expression library, said method comprising:

processing a biological sample comprising a source antibody gene pool so as to isolate a plurality of nucleic acids, the plurality of the nucleic acids encoding a naturally occurring antibody repertoire, followed by an amplification of the plurality of the nucleic acids, introducing a specific tri-nucleotide sequence marker in a portion of the nucleic acid encoding a heavy chain of a naturally occurring antibody so as to catalogue the nucleic acid to the source antibody gene pool, and to enable tracing of displayed antibodies back to the source antibody gene pool, wherein the tri-nucleotide sequence marker is introduced through the amplification of the nucleic acid by one or more degenerate primers selected from the group consisting of SEQ ID NO:1 to SEQ ID NO: 68, wherein the one or more degenerate primers include the specific tri-nucleotide marker that is specific to the source antibody gene pool, pooling of the amplified nucleic acids from separate amplifications, each of the nucleic acids having the tri-nucleotide sequence marker, so as to obtain pooled amplified nucleic acids, and cloning of the pooled amplified nucleic acids into one or more phagemid vectors, displaying of the antibodies on a surface of at least one phage so as to obtain the displayed antibodies, the displaying is optionally followed by a screening of the displayed antibodies against a specific antigen so as to remove an antibody non-binder to the specific antigen and to obtain a screened antibody molecule;

transferring the nucleic acid of the displayed antibody or the screened antibody molecule into a yeast for display of said antibody molecules on a surface of the yeast so as to obtain a yeast-displayed antibody, wherein the transferring is optionally followed by a screening of the yeast-displayed antibodies against a specific antigenic target; and a) selecting or isolating the nucleic acid of the yeast displayed antibodies showing desired functional properties to form a naïve monoclonal antibody gene expression library, or b) selecting or isolating the nucleic acid of the yeast displayed antibodies showing higher affinity to the target antigen to form the screened naïve monoclonal antibody gene expression library.

2. The method as claimed in claim 1,
wherein the biological sample is selected from the group consisting of a blood sample and any samples expressing antibody genes,
wherein the biological sample is obtained from selected healthy donors or subjects,
wherein a criteria of the selection is based on a diversity in language spoken, ethnicity, or a geographical location of said donors or subjects, and
wherein the subjects are human.

3. The method as claimed in claim 1,
wherein the processing of the biological sample involves isolating from a blood sample, peripheral blood mononuclear cells selected from the group consisting of lymphocytes, monocytes, platelets, granulocytes, and any combination thereof, followed by estimating a naïve B-cell population therein through flow-cytometry,
wherein the estimation of the naïve B-cell population is carried out by identifying differential expression of cell surface or intracellular markers selected from the group consisting of IgD, CD20, CD19, CD27, CD24, CD38, and any combination thereof, and
wherein the naïve B-cell population in a range from about 10% to about 15% of total peripheral blood mononuclear cells is obtained.

4. The method as claimed in claim 1, wherein the isolation of the nucleic acid includes isolating of a m-RNA, followed by a c-DNA generation.

5. The method as claimed in claim 1, wherein the amplification involves a primary PCR amplification followed by a secondary PCR amplification by employing any one of degenerate primers or combinations thereof set forth as SEQ ID NO: 1 to SEQ ID NO: 68.

6. The method as claimed in claim 5, wherein the PCR amplification is carried out for about 18 cycles to about 25 cycles, each cycle with a denaturation for about 1 minute to about 2 minutes at about 94° C. followed by an annealing for about 1 minute to about 2 minutes at about 50° C. and an extension for about 50 seconds to about 90 seconds at about 72° C., and wherein the PCR products obtained post amplification are optionally purified.

7. The method as claimed in claim 1, wherein the cloning into the phagemid vector and yeast involves an antibody light chain cloning followed by an antibody heavy chain cloning, both with a transformation efficiency of about $10^8$; and wherein the cloning yields an estimated number of the nucleic acids in a range of $10^{10}$ to about $10^{11}$ pfu/mL.

8. The method as claimed in claim 1,
wherein the screening of the displayed antibodies so as to obtain a screened library involves a panning with an antigen coated on a magnetic bead so as to isolate an antibody of interest, and
wherein said phage display screening/panning is employed so as to remove the antibody non-binder.

9. The method as claimed in claim 1, wherein the antibody format is selected from the group consisting of Fab and ScFv.

10. The method as claimed in claim 1, wherein the screening of the yeast-displayed antibody is carried out by employing at least one entity selected from the group consisting of a competing antigenic epitope, an antibody paratope conformation, an antibody paratope sequence, an antibody paratope sequence motif, and any combination thereof, so as to isolate a Fab or a ScFv molecule using a protease cleavage site selected from the group consisting of Tobacco Etch Virus (TEV), Enterokinase, Thrombin, Factor X a, HRV 3C protease, a similar protease cleavage protein, and any combination thereof.

11. The method as claimed in claim 1, wherein the display of antibody molecules on the surface of the yeast includes: isolating of a plasmid DNA from a phage library followed by digesting of the plasmid DNA by restriction digestion, cloning, and transforming into a haploid yeast cell or into a diploid yeast cell through a mating of two haploid yeast cells.

12. The method as claimed in claim 1, wherein the transferring is carried out by a transforming of the nucleic acid of the displayed antibodies or the screened antibody molecules into the plurality of the yeast, with transformation efficiency of about $10^8$.

13. The method as claimed in claim 1, wherein the screening to obtain the yeast-displayed antibodies is employed so as to execute an affinity based selection, and so as to obtain antibody binders.

14. The method as claimed in claim 1, wherein the antibodies or genes are selected based on binding of the antibodies with the antigenic target by employing techniques or technologies selected from the group consisting of flow cytometry, ELISA, bead based detection platforms, imaging, SPR, and any combination thereof.

15. The method as claimed in claim 1, wherein the naïve antibody library is a collection of the antibodies or genes of the antibodies expressed on the surface of the yeast, or is a collection of the nucleic acids of the antibodies isolated from the yeast, and wherein the naïve antibody library comprises clones in a range from about $10^7$ to about $10^9$.

16. A naïve monoclonal antibody gene expression library obtained by the method of claim 1.

17. The naïve antibody library of claim 16, wherein the library is obtained by amplifying the nucleic acid isolated from the biological sample by using any of primer sequences set forth as SEQ ID NO:1 to SEQ ID NO: 68.

18. The naïve antibody library as claimed in claim 17, wherein the primer sequence encompasses the trinucleotide sequence tag that catalogues the antibody genes to a respective geographical location where the biological sample was obtained, which enables a tracing of the antibody genes back to the source antibody gene pool.

19. A method for treating at least one disease selected from the group consisting of cancer, rheumatoid arthritis, neurological disorders, infectious diseases, and metabolic disorders; using as diagnostics or as prognostics of the at least one disease; and using for research purposes, target discovery, validation in functional genomics, or any application where antibodies or derivatives of antibodies are employed, the method comprising:

obtaining an antibody from at least one library selected from the group consisting of the naïve monoclonal antibody gene expression library, and a screened naïve antibody library, according to the method of claim 1.

* * * * *

```
                        SEQUENCE LISTING

<160> NUMBER OF SEQ ID NOS: 68

<210> SEQ ID NO 1
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: Forward Primer- HuVH1B/7A

<400> SEQUENCE: 1
gtcctcgcaa ctccatggat ggcccagrtg cagctggtgc artctgg                47

<210> SEQ ID NO 2
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH1C

<400> SEQUENCE: 2
gtcctcgcaa ctccatggat ggccsaggtc cagctggtrc agtctgg                47

<210> SEQ ID NO 3
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH2B

<400> SEQUENCE: 3
gtcctcgcaa ctccatggat ggcccagrtc accttgaagg agtctgg                47

<210> SEQ ID NO 4
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH3B

<400> SEQUENCE: 4
gtcctcgcaa ctccatggat ggccsaggtg cagctggtgg agtctgg                47

<210> SEQ ID NO 5
<211> LENGTH: 47
<212> TYPE: DNA
```

```
<213> ORGANISM: Homo sapiens
<220> FEATURE:
<221> NAME/KEY: primer_bind
<222> LOCATION: (1)..(47)
<223> OTHER INFORMATION: forward primer - HuVH3C

<400> SEQUENCE: 5
gtcctcgcaa ctccatggat ggccgaggtg cagctggtgg agwcygg        47

<210> SEQ ID NO 6
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH4B

<400> SEQUENCE: 6
gtcctcgcaa ctccatggat ggcccaggtg cagctacagc agtgggg        47

<210> SEQ ID NO 7
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH4C

<400> SEQUENCE: 7
gtcctcgcaa ctccatggat ggcccagstg cagctgcagg agtcsgg        47

<210> SEQ ID NO 8
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH5B

<400> SEQUENCE: 8
gtcctcgcaa ctccatggat ggccgargtg cagctggtgc agtctgg        47

<210> SEQ ID NO 9
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH6A

<400> SEQUENCE: 9
gtcctcgcaa ctccatggat ggcccaggta cagctgcagc agtcagg        47

<210> SEQ ID NO 10
<211> LENGTH: 42
<212> TYPE: DNA
<213> ORGANISM: Homo sapiens
<220> FEATURE:
<221> NAME/KEY: primer_bind
<222> LOCATION: (1)..(42)
<223> OTHER INFORMATION: reverse primer- HuJH1/2

<400> SEQUENCE: 10
accgcctcca cctctagatg aggagacggt gaccagggtg cc        42
```

<210> SEQ ID NO 11
<211> LENGTH: 42
<212> TYPE: DNA
<213> ORGANISM: Homo sapiens
<220> FEATURE:
<221> NAME/KEY: primer_bind
<222> LOCATION: (1)..(42)
<223> OTHER INFORMATION: reverse primer- HuJH3

<400> SEQUENCE: 11
accgcctcca cctctagatg aagagacggt gaccattgtc cc                              42

<210> SEQ ID NO 12
<211> LENGTH: 42
<212> TYPE: DNA
<213> ORGANISM: Homo sapiens
<220> FEATURE:
<221> NAME/KEY: primer_bind
<222> LOCATION: (1)..(42)
<223> OTHER INFORMATION: reverse primer- HuJH4/5

<400> SEQUENCE: 12
accgcctcca cctctagatg aggagacggt gaccagggtt cc                              42

<210> SEQ ID NO 13
<211> LENGTH: 42
<212> TYPE: DNA
<213> ORGANISM: Homo sapiens
<220> FEATURE:
<221> NAME/KEY: primer_bind
<222> LOCATION: (1)..(42)
<223> OTHER INFORMATION: reverse primer- HuJH6

<400> SEQUENCE: 13
accgcctcca cctctagatg aggagacggt gaccgtggtc cc                              42

<210> SEQ ID NO 14
<211> LENGTH: 42
<212> TYPE: DNA
<213> ORGANISM: Homo sapiens
<220> FEATURE:
<221> NAME/KEY: primer_bind
<222> LOCATION: (1)..(42)
<223> OTHER INFORMATION: reverse primer- HuJH1/2

<400> SEQUENCE: 14
accgcctcca cctctagatg aggagacggt caccagggtg cc                              42

<210> SEQ ID NO 15
<211> LENGTH: 42
<212> TYPE: DNA
<213> ORGANISM: Homo sapiens
<220> FEATURE:
<221> NAME/KEY: primer_bind
<222> LOCATION: (1)..(42)
<223> OTHER INFORMATION: reverse primer- HuJH3

<400> SEQUENCE: 15
accgcctcca cctctagatg aagagacggt caccattgtc cc                              42

<210> SEQ ID NO 16
<211> LENGTH: 42
<212> TYPE: DNA
<213> ORGANISM: Homo sapiens
<220> FEATURE:
<221> NAME/KEY: primer_bind
<222> LOCATION: (1)..(42)

<223> OTHER INFORMATION: reverse primer- HuJH4/5

<400> SEQUENCE: 16
accgcctcca cctctagatg aggagacggt caccagggtt cc                               42

<210> SEQ ID NO 17
<211> LENGTH: 42
<212> TYPE: DNA
<213> ORGANISM: Homo sapiens
<220> FEATURE:
<221> NAME/KEY: primer_bind
<222> LOCATION: (1)..(42)
<223> OTHER INFORMATION: reverse primer- HuJH6

<400> SEQUENCE: 17
accgcctcca cctctagatg aggagacggt caccgtggtc cc                               42

<210> SEQ ID NO 18
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH1B/7A

<400> SEQUENCE: 18
gtcctcgcaa ctccatggat ggcgcagrtg cagctggtgc artctgg                          47

<210> SEQ ID NO 19
<211> LENGTH: 46
<212> TYPE: DNA
<213> ORGANISM: Homo sapiens
<220> FEATURE:
<221> NAME/KEY: primer_bind
<222> LOCATION: (1)..(46)
<223> OTHER INFORMATION: forward primer-HuVH1C

<400> SEQUENCE: 19
tcctcgcaac tccatggatg gcgsaggtcc agctggtrca gtctgg                           46

<210> SEQ ID NO 20
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH2B

<400> SEQUENCE: 20
gtcctcgcaa ctccatggat ggcgcagrtc accttgaagg agtctgg                          47

<210> SEQ ID NO 21
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH3B

<400> SEQUENCE: 21
gtcctcgcaa ctccatggat ggcgsaggtg cagctggtgg agtctgg                          47

<210> SEQ ID NO 22
<211> LENGTH: 47

```
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH3C

<400> SEQUENCE: 22
gtcctcgcaa ctccatggat ggcggaggtg cagctggtgg agwcygg       47

<210> SEQ ID NO 23
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH4B

<400> SEQUENCE: 23
gtcctcgcaa ctccatggat ggcgcaggtg cagctacagc agtgggg       47

<210> SEQ ID NO 24
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH4C

<400> SEQUENCE: 24
gtcctcgcaa ctccatggat ggcgcagstg cagctgcagg agtcsgg       47

<210> SEQ ID NO 25
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH5B

<400> SEQUENCE: 25
gtcctcgcaa ctccatggat ggcggargtg cagctggtgc agtctgg       47

<210> SEQ ID NO 26
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH6A

<400> SEQUENCE: 26
gtcctcgcaa ctccatggat ggcgcaggta cagctgcagc agtcagg       47

<210> SEQ ID NO 27
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH1B/7A

<400> SEQUENCE: 27
```
gtcctcgcaa ctccatggat ggcacagrtg cagctggtgc artctgg                          47

<210> SEQ ID NO 28
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH1C

<400> SEQUENCE: 28
gtcctcgcaa ctccatggat ggcasaggtc cagctggtrc agtctgg                          47

<210> SEQ ID NO 29
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH2B

<400> SEQUENCE: 29
gtcctcgcaa ctccatggat ggcacagrtc accttgaagg agtctgg                          47

<210> SEQ ID NO 30
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH3B

<400> SEQUENCE: 30
gtcctcgcaa ctccatggat ggcasaggtg cagctggtgg agtctgg                          47

<210> SEQ ID NO 31
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH3C

<400> SEQUENCE: 31
gtcctcgcaa ctccatggat ggcagaggtg cagctggtgg agwcygg                          47

<210> SEQ ID NO 32
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH4B

<400> SEQUENCE: 32
gtcctcgcaa ctccatggat ggcacaggtg cagctacagc agtgggg                          47

<210> SEQ ID NO 33
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH4C

<400> SEQUENCE: 33
gtcctcgcaa ctccatggat ggcacagstg cagctgcagg agtcsgg       47

<210> SEQ ID NO 34
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH5B

<400> SEQUENCE: 34
gtcctcgcaa ctccatggat ggcagargtg cagctggtgc agtctgg       47

<210> SEQ ID NO 35
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH6A

<400> SEQUENCE: 35
gtcctcgcaa ctccatggat ggcacaggta cagctgcagc agtcagg       47

<210> SEQ ID NO 36
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH1B/7A

<400> SEQUENCE: 36
gtcctcgcaa ctccatggat ggctcagrtg cagctggtgc artctgg       47

<210> SEQ ID NO 37
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer-HuVH1C

<400> SEQUENCE: 37
gtcctcgcaa ctccatggat ggctsaggtc cagctggtrc agtctgg       47

<210> SEQ ID NO 38
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH2B

<400> SEQUENCE: 38
gtcctcgcaa ctccatggat ggctcagrtc accttgaagg agtctgg       47

<210> SEQ ID NO 39

```
<210> SEQ ID NO 39
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH3B

<400> SEQUENCE: 39
gtcctcgcaa ctccatggat ggctsaggtg cagctggtgg agtctgg          47

<210> SEQ ID NO 40
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH3C

<400> SEQUENCE: 40
gtcctcgcaa ctccatggat ggctgaggtg cagctggtgg agwcygg          47

<210> SEQ ID NO 41
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH4B

<400> SEQUENCE: 41
gtcctcgcaa ctccatggat ggctcaggtg cagctacagc agtgggg          47

<210> SEQ ID NO 42
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH4C

<400> SEQUENCE: 42
gtcctcgcaa ctccatggat ggctcagstg cagctgcagg agtcsgg          47

<210> SEQ ID NO 43
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH5B

<400> SEQUENCE: 43
gtcctcgcaa ctccatggat ggctgargtg cagctggtgc agtctgg          47

<210> SEQ ID NO 44
<211> LENGTH: 47
<212> TYPE: DNA
<213> ORGANISM: Homo sapiens
<220> FEATURE:
<221> NAME/KEY: primer_bind
<222> LOCATION: (1)..(47)
<223> OTHER INFORMATION: forward primer- HuVH6A

<400> SEQUENCE: 44
```
gtcctcgcaa ctccatggat ggctcaggta cagctgcagc agtcagg       47

<210> SEQ ID NO 45
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVk1B

<400> SEQUENCE: 45
accgcctcca ccaagcttga catccagwtg acccagtctc c       41

<210> SEQ ID NO 46
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVk2

<400> SEQUENCE: 46
accgcctcca ccaagcttga tgttgtgatg actcagtctc c       41

<210> SEQ ID NO 47
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVk3B

<400> SEQUENCE: 47
accgcctcca ccaagcttga aattgtgwtg acrcagtctc c       41

<210> SEQ ID NO 48
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVk4B

<400> SEQUENCE: 48
accgcctcca ccaagcttga tattgtgatg acccacactc c       41

<210> SEQ ID NO 49
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVk5

<400> SEQUENCE: 49
accgcctcca ccaagcttga aacgacactc acgcagtctc c       41

<210> SEQ ID NO 50
<211> LENGTH: 41
<212> TYPE: DNA
<213> ORGANISM: Homo sapiens
<220> FEATURE:

```
<221> NAME/KEY: primer_bind
<222> LOCATION: (1)..(41)
<223> OTHER INFORMATION: forward primer- HuVk6

<400> SEQUENCE: 50
accgcctcca ccaagcttga aattgtgctg actcagtctc c                41

<210> SEQ ID NO 51
<211> LENGTH: 44
<212> TYPE: DNA
<213> ORGANISM: Homo sapiens
<220> FEATURE:
<221> NAME/KEY: primer_bind
<222> LOCATION: (1)..(44)
<223> OTHER INFORMATION: reverse primer- Hu Jk1

<400> SEQUENCE: 51
accgcctcca ccggcgcgcc acgtttgatt tccaccttgg tccc             44

<210> SEQ ID NO 52
<211> LENGTH: 44
<212> TYPE: DNA
<213> ORGANISM: Homo sapiens
<220> FEATURE:
<221> NAME/KEY: primer_bind
<222> LOCATION: (1)..(44)
<223> OTHER INFORMATION: reverse primer- HuJk2

<400> SEQUENCE: 52
accgcctcca ccggcgcgcc acgtttgatc tccagcttgg tccc             44

<210> SEQ ID NO 53
<211> LENGTH: 44
<212> TYPE: DNA
<213> ORGANISM: Homo sapiens
<220> FEATURE:
<221> NAME/KEY: primer_bind
<222> LOCATION: (1)..(44)
<223> OTHER INFORMATION: reverse primer- HuJk3

<400> SEQUENCE: 53
accgcctcca ccggcgcgcc acgtttgata tccactttgg tccc             44

<210> SEQ ID NO 54
<211> LENGTH: 44
<212> TYPE: DNA
<213> ORGANISM: Homo sapiens
<220> FEATURE:
<221> NAME/KEY: primer_bind
<222> LOCATION: (1)..(44)
<223> OTHER INFORMATION: reverse primer- HuJk4

<400> SEQUENCE: 54
accgcctcca ccggcgcgcc acgtttgatc tccaccttgg tccc             44

<210> SEQ ID NO 55
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVl1A

<400> SEQUENCE: 55
accgcctcca ccaagcttca gtctgtgctg actcagccac c                41
```

<210> SEQ ID NO 56
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVl1B

<400> SEQUENCE: 56
accgcctcca ccaagcttca gtctgtgytg acgcagccgc c                41

<210> SEQ ID NO 57
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVl1C

<400> SEQUENCE: 57
accgcctcca ccaagcttca gtctgtcgtg acgcagccgc c                41

<210> SEQ ID NO 58
<211> LENGTH: 39
<212> TYPE: DNA
<213> ORGANISM: Homo sapiens
<220> FEATURE:
<221> NAME/KEY: primer_bind
<222> LOCATION: (1)..(39)
<223> OTHER INFORMATION: forward primer- HuVl2

<400> SEQUENCE: 58
accgcctcca ccaagcttca rtctgccctg actcagcct                  39

<210> SEQ ID NO 59
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVl3A

<400> SEQUENCE: 59
accgcctcca ccaagctttc ctatgwgctg actcagccac c                41

<210> SEQ ID NO 60
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVl3B

<400> SEQUENCE: 60
accgcctcca ccaagctttc ttctgagctg actcaggacc c                41

<210> SEQ ID NO 61
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVl4

```
<400> SEQUENCE: 61
accgcctcca ccaagcttca cgttatactg actcaaccgc c                              41

<210> SEQ ID NO 62
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVl5

<400> SEQUENCE: 62
accgcctcca ccaagcttca ggctgtgctg actcagccgt c                              41

<210> SEQ ID NO 63
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVl6

<400> SEQUENCE: 63
accgcctcca ccaagcttaa ttttatgctg actcagcccc a                              41

<210> SEQ ID NO 64
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVl7/8

<400> SEQUENCE: 64
accgcctcca ccaagcttca grctgtggtg acycaggagc c                              41

<210> SEQ ID NO 65
<211> LENGTH: 41
<212> TYPE: DNA
<213> ORGANISM: Homo sapiens
<220> FEATURE:
<221> NAME/KEY: primer_bind
<222> LOCATION: (1)..(41)
<223> OTHER INFORMATION: forward primer- HuVl9

<400> SEQUENCE: 65
accgcctcca ccaagcttcw gcctgtgctg actcagccmc c                              41

<210> SEQ ID NO 66
<211> LENGTH: 44
<212> TYPE: DNA
<213> ORGANISM: Homo sapiens
<220> FEATURE:
<221> NAME/KEY: primer_bind
<222> LOCATION: (1)..(44)
<223> OTHER INFORMATION: reverse primer- HuJ1-1

<400> SEQUENCE: 66
accgcctcca ccggcgcgcc acctaggacg gtgaccttgg tccc                           44

<210> SEQ ID NO 67
<211> LENGTH: 44
<212> TYPE: DNA
<213> ORGANISM: Homo sapiens
```

```
<220> FEATURE:
<221> NAME/KEY: primer_bind
<222> LOCATION: (1)..(44)
<223> OTHER INFORMATION: reverse primer- HuJ1_2-3

<400> SEQUENCE: 67
accgcctcca ccggcgcgcc acctaggacg gtcagcttgg tccc            44

<210> SEQ ID NO 68
<211> LENGTH: 44
<212> TYPE: DNA
<213> ORGANISM: Homo sapiens
<220> FEATURE:
<221> NAME/KEY: primer_bind
<222> LOCATION: (1)..(44)
<223> OTHER INFORMATION: reverse primer- HuJ1_4-5

<400> SEQUENCE: 68
accgcctcca ccggcgcgcc acctaaaacg gtgagctggg tccc            44
```